United States Patent
Chaturvedula et al.

(10) Patent No.: US 7,049,323 B2
(45) Date of Patent: May 23, 2006

(54) AMIDOHETEROCYCLES AS MODULATORS OF THE MELANOCORTIN-4 RECEPTOR

(75) Inventors: Prasad V. Chaturvedula, Cheshire, CT (US); Guanglin Luo, Madison, CT (US); Shikha Vig, Durham, CT (US); Graham S. Poindexter, Old Saybrook, CT (US); Brett R. Beno, Cromwell, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 67 days.

(21) Appl. No.: 10/813,870

(22) Filed: Mar. 30, 2004

(65) Prior Publication Data

US 2004/0224901 A1    Nov. 11, 2004

Related U.S. Application Data

(60) Provisional application No. 60/465,552, filed on Apr. 25, 2003.

(51) Int. Cl.
*C07D 401/02*    (2006.01)
*A61K 31/44*    (2006.01)

(52) U.S. Cl. ............ 514/307; 514/210.01; 514/252.13; 514/422; 514/423; 544/359; 546/139; 548/517; 548/518

(58) Field of Classification Search ........... 514/210.01, 514/252.13, 307, 422, 423; 546/139; 548/517, 548/518; 544/359
See application file for complete search history.

(56) References Cited

FOREIGN PATENT DOCUMENTS

| | | |
|---|---|---|
| WO | WO 99/64002 | 12/1999 |
| WO | WO 00/74679 A1 | 12/2000 |
| WO | WO 01/70337 A1 | 9/2001 |
| WO | WO 01/70708 A1 | 9/2001 |
| WO | WO 01/91752 A1 | 12/2001 |
| WO | WO 02/15909 A1 | 2/2002 |
| WO | WO 02/066869 A1 | 8/2002 |
| WO | WO 02/068387 A2 | 9/2002 |
| WO | WO 02/068388 A2 | 9/2002 |
| WO | WO 02/070511 A1 | 9/2002 |
| WO | WO 02/079146 A2 | 10/2002 |
| WO | WO 03/007949 A1 | 1/2003 |

*Primary Examiner*—Zinna Northington Davis
(74) *Attorney, Agent, or Firm*—James Epperson

(57) ABSTRACT

Novel azetidinyl and pyrrolidinyl compounds are ligands of melanocortin-4 receptors and are useful for treating conditions responsive to the modulation of melanocortin-4 receptors such as obesity, diabetes, and sexual dysfunction.

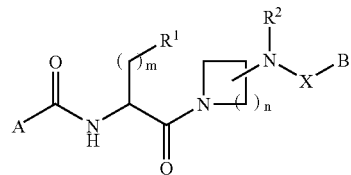

10 Claims, No Drawings

AMIDOHETEROCYCLES AS MODULATORS OF THE MELANOCORTIN-4 RECEPTOR

CROSS REFERENCE TO RELATED APPLICATIONS

This application claims priority to U.S. provisional application 60/465,552, filed Apr. 25, 2003.

BACKGROUND OF THE INVENTION

This invention relates to compounds useful in treating diseases responsive to the activation of melanocortin receptors, particularly the melanocortin-4 receptor (MC4R), to methods of treating such diseases, and to pharmaceutical compositions comprising same.

Melanocortin peptides, particularly α-melanocyte stimulating hormone (α-MSH), are known to have a wide range of effects on biological functions including feeding behavior, pigmentation, exocrine and sexual function (MacNeil et al *Eur. J. Pharmacol.* 2002, 440, 141–157; Chiesi, M et al. *Trends Pharm. Sci.* 2001, 22, 247–254; Wikberg, J. E. S et al. *Pharm. Res.* 2000, 42, 393–420; Wikberg, J. E. S. *Eur. J. Pharmacol.* 1999, 375, 295–310; and Vergoni, A. V. and Bertolini, A. *Eur. J. Pharmacol.* 2000, 405, 25–32).

The biological effects of α-MSH are mediated by a sub-family of G protein-coupled receptors, termed melanocortin receptors. There are four melanocortin receptors: MC1R, MC3R, MC4R, and MC5R (MC2R is not a α-MSH receptor but is the adrenocorticotropic hormone (ACTH) receptor; MCXR denotes a generic term for the melanocortin receptors). Activating any one of these receptors results in the stimulation of cAMP formation.

MC1R was first found in melanocytes. Naturally occurring inactive variants of MC1R in animals were shown to lead to alterations in pigmentation and a subsequent lighter coat color. MC3R is expressed in the brain and peripheral tissues, and knockout studies have revealed that MC3R is responsible for alterations in feeding behavior and body weight. MC4R is primarily expressed in the brain. Genetic knock-outs and pharmacologic manipulation of MC4R in animals have shown that agonizing MC4R causes weight loss and antagonizing MC4R produces weight gain. MC5R is ubiquitously expressed in many peripheral tissues and in the brain, but its expression is greatest in exocrine glands. Genetic knock-out of this receptor in mice results in altered regulation of exocrine gland function, leading to changes in water repulsion and thermoregulation.

Evidence for the involvement of melanocortin receptors in obesity includes studies in the agouti mouse. The viable yellow variants of agouti mice ($A^{vy}$) express the agouti protein both ectopically and within the hair follicle. The agouti protein acts as an antagonist of the MC1R, MC3R, and MC4R receptors. These mice are characterized by maturity-onset obesity, hyperinsulinemia, hyperglycemia in males, yellow coat color, hyperphagia, increased rates of hepatic lipogenesis and decreased rates of lipolysis in indicating that blocking the action of the MC1R, MC3R, and MC4R can lead to the characteristics of the pleiotropic obesity syndrome [Yen, T. T. et al *FASEB J.* 1994, 8, 479–488].

MC4R knockout mice exhibit the same phenotype as the agouti mice ($A^{vy}$) and have other characteristics of the pleiotropic obesity syndrome described above [Huszar, D. et al *Cell* 1997, 88, 131–141]. Rodents injected intracerebroventricularly (ICV) with the cyclic heptapeptide melanotan-II (MT-II), an agonist for the MC1R, MC3R, MC4R, and MC5R receptors, have reduced food intake in several animal feeding models (NPY, ob/ob, agouti, fasted) while ICV injected SHU-9119, a MC3R/MC4R antagonist and MC1R/MC5R agonist, reverses this effect and can induce hyperphagia [PCT WO 99/64002 (Merck)]. Additionally, chronic intraperitoneal treatment of Zucker fatty rats with an α-NDP-MSH derivative (HP228) has been reported to activate MC1R, MC3R, MC4R and MC5R receptors and to attenuate food intake and body weight gain over a 12 week.

Melanocortin receptors may also be viable targets for the control of certain types of sexual dysfunction. Intramuscular administration of melanotan-II (MT-II) within a dose range of 0.005–0.03 mg/kg caused intermittent non-painful penile erections in three normal male volunteers for a period of 1–5 hours after dosing [Dorr, R. T. et al. *Life Sciences* 1996, 58, 1777–1784. Subcutaneous administration of MT-II (0.025 mg/kg and 0.1 mg/kg) to 10 patients with psychogenic erectile dysfunction caused transient erections (8 responders) with onset from 50–180 min [Wessells, H. et al *J. Urology* 1998, 160, 389–393].

Several publications have disclosed melanocortin receptor ligands. The compounds of this invention are distinct from and are not suggested by these publications.

Much attention has been focused in the patent literature on melanocortin agonists and their use in treating body weight and sexual disorders [Andersson et al. *Exp. Opin. Ther. Patents* 2001, 11, 1583–1592]. The first reported non-peptidic melanocortin agonist is shown below. It was isolated from a plant extract from the genus *Trichocaulon* or *Hoodia* [WO 98/46243, Quandrant Holdings].

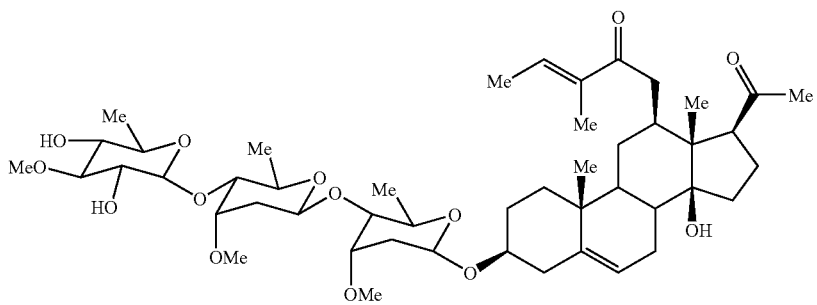

PCT WO 98/46243 (Quandrant Holdings)

Trega Biosciences has reported a series of aromatic amine structures which have bicyclic terminal groups, typically tetrahydroisoquinolines, and are active at MC3R and MC4R [PCT WO 99/55679]. A typical structure is shown below.

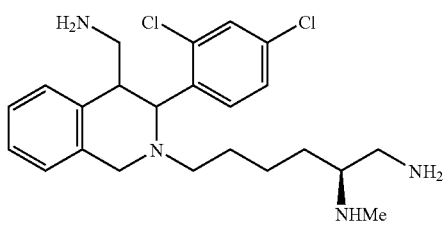

PCT WO 99/55679 (Triega Biosciences)

More recently, three patent applications form Melacure Tharapeutics AB disclose a series of indolic amides and guanidines as modulators of MCXR for the treatment of obesity, anorexia, and inflammation [PCT WO 01/55106; PCT WO 01/55107; and PCT WO 01/55109] and are exemplified by the structures shown below.

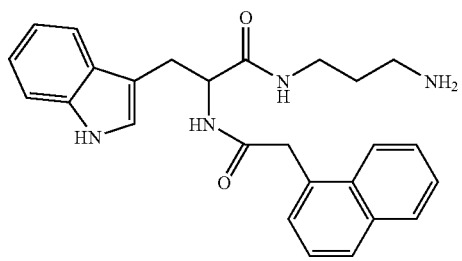

PCT WO 01/55106 (Melacure)

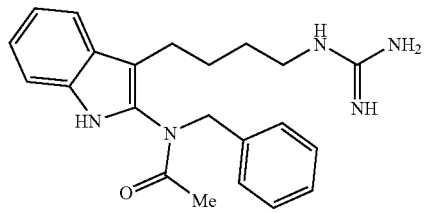

PCT WO 01/55107 (Melacure)

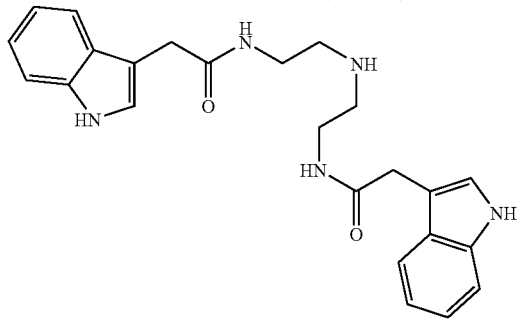

PCT WO 01/55109 (Melacure)

Melacure also discloses the use of benzylideneaminoguanidines and hydroxyguanidines as melanocortin receptor ligands [PCT WO 02/11715 and PCT WO 02/12178]. Typical structures disclosed in the applications are shown below.

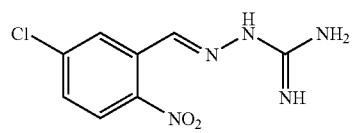

PCT WO 02/11715 (Melacure)

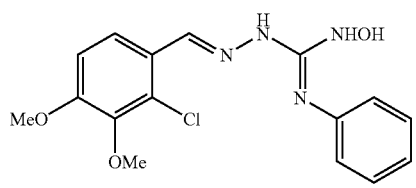

PCT WO 02/12178 (Melacure)

Seven PCT applications from Merck & Co. have disclosed a series of substituted piperidine MC4R agonists useful in the treatment of obesity and sexual dysfunction [PCT WO 99/64002; PCT WO00/74679; PCT WO01/70337; PCT WO10/70708; PCT WO 01/91752; PCT WO02/15909, and PCT WO 03/007949 A1]. The structures in these applications are exemplified below.

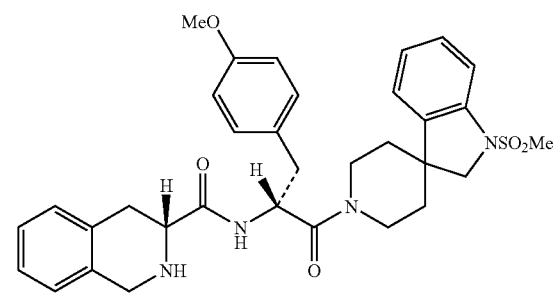

PCT WO 99/64002 (Merck)

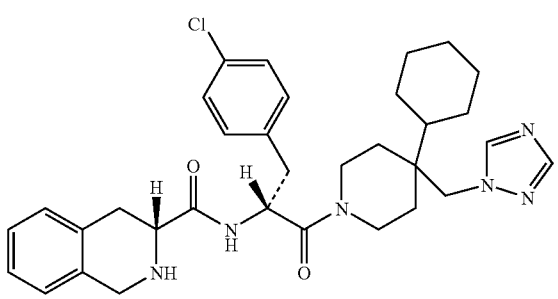

PCT WO 00/74679 (Merck)

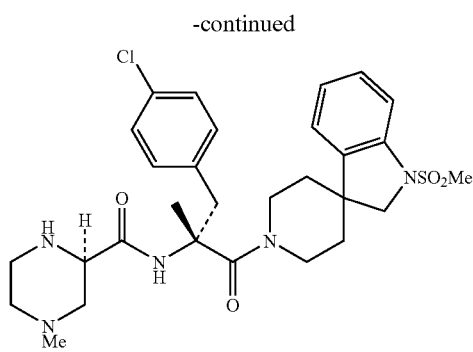
PCT WO 01/70337 (Merck)
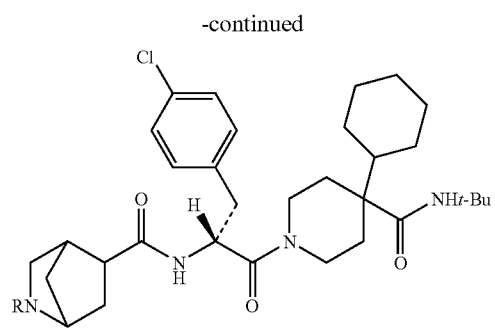
PCT WO 03/007949 (Merck)
Three additional patent applications have appeared from Merck (PCT WO 02/067869; 02/068387; and 02/063388) and are exemplified by structures shown below.
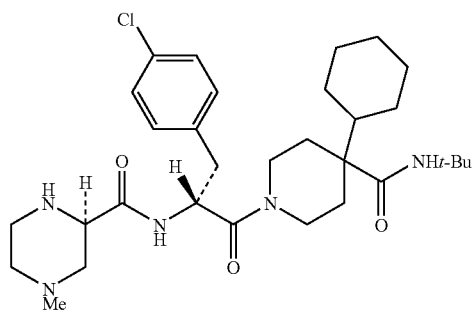
PCT WO 01/70708 (Merck)
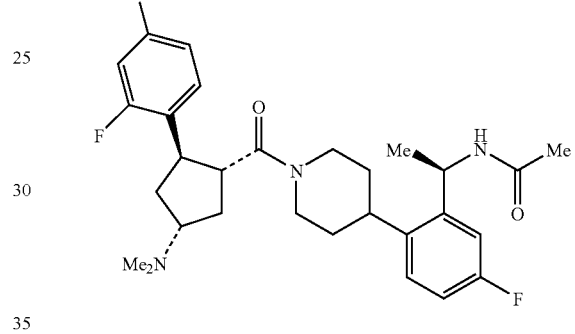
PCT WO 02/066869 (Merck)
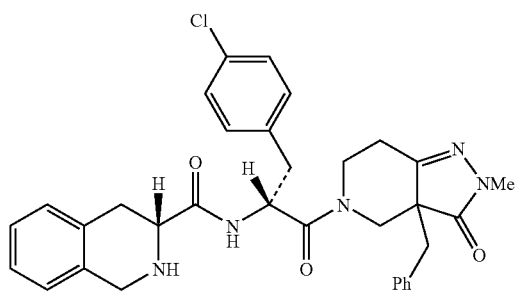
PCT WO 01/91752 (Merck)
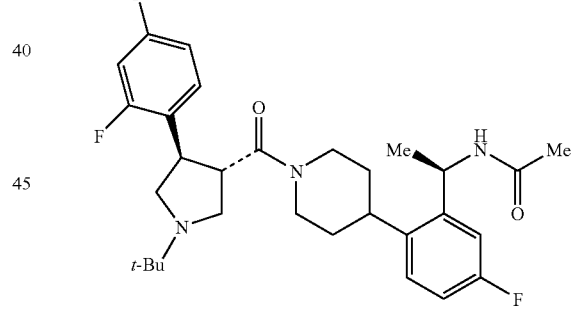
PCT WO 02/068388 (Merck)
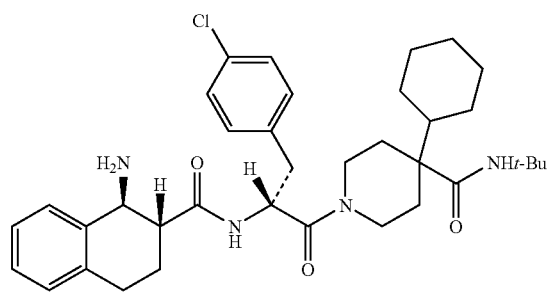
PCT WO 02/15909 (Merck)
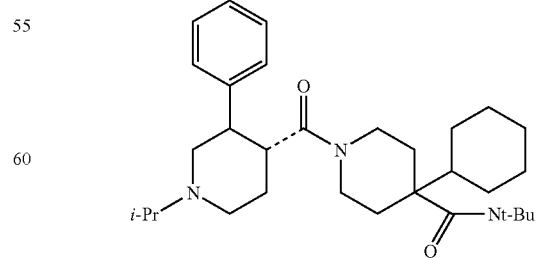
PCT WO 02/068387 (Merck)

Pfizer has also recently disclosed a number of MC4R agonists [PCT WO/02/00654].

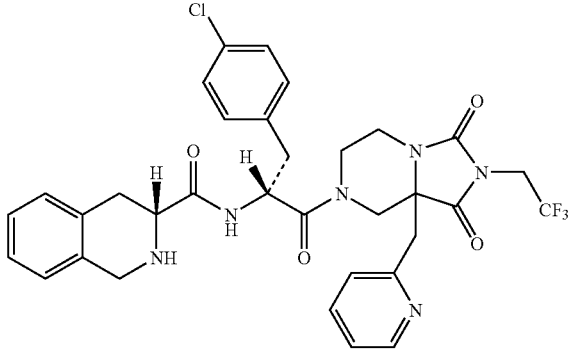

PCT WO 02/00654 (Pfizer)

A recent Chiron application has appeared which discloses a series of heterocyclic guanidine derivatives (PCT WO 02/082443).

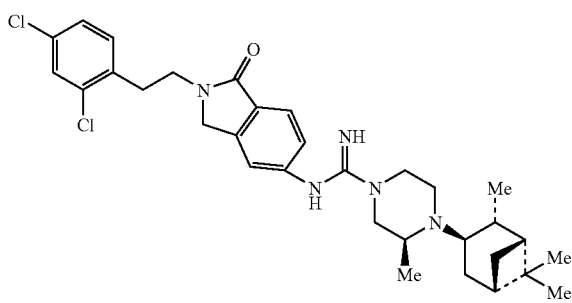

PCT WO 02/81443 (Chiron)

Two PCT publications from Bristol Myers Squibb have been published and the generic structures are shown below (WO 02/079146 A2 and WO 02/070511 A1).

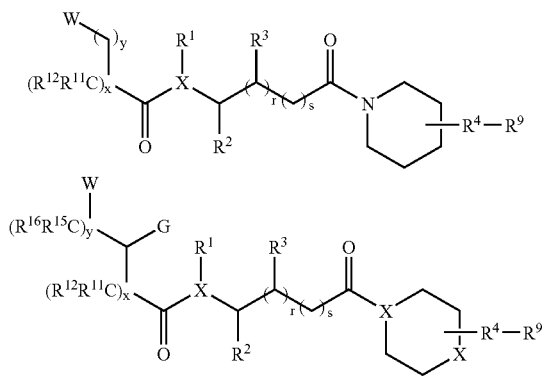

SUMMARY OF THE INVENTION

The present invention relates to novel amidoazetidine and amidopyrrolidine derivatives and their salts having the general formula I

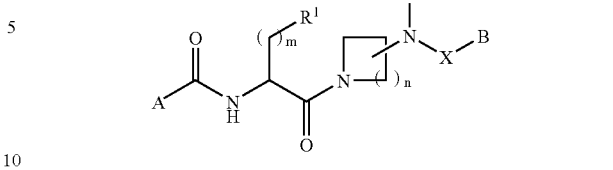

wherein A, B, X, $R_1$, $R_2$, m, and n, are defined below. The invention also provides pharmaceutical compositions comprising said derivatives and a pharmaceutically acceptable carrier or diluent and a method of treating or preventing diseases and disorders responsive to the activation or inhibition of the melanocortin receptors in mammals.

DETAILED DESCRIPTION OF THE INVENTION

This invention comprises compounds of Formula I

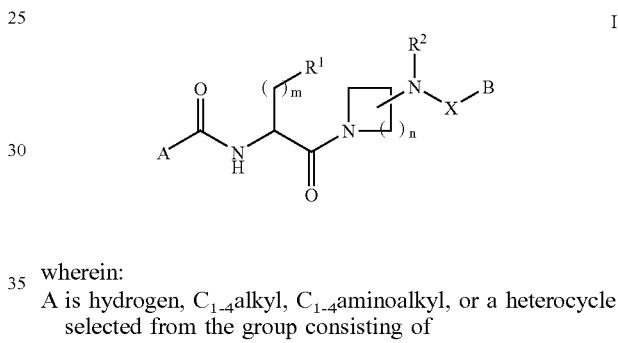

wherein:
A is hydrogen, $C_{1-4}$alkyl, $C_{1-4}$aminoalkyl, or a heterocycle selected from the group consisting of

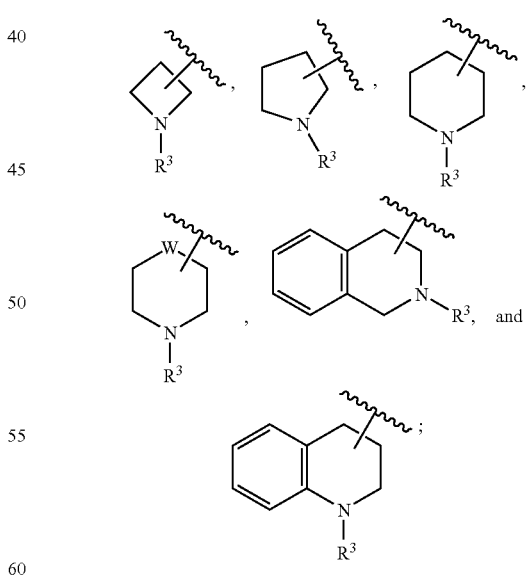

W is $NR^3$, O, or S;
$R^1$ is selected from phenyl, naphthyl, benzfuranyl, benzthienyl, and indolyl moieties that are unsubstituted or substituted with 1 to 2 substituents selected from halo, alkyl, alkyloxy, cyano, trifluoromethyl, and alkoxycarbonyl;
$R^2$ is $C_{1-6}$alkyl or $C_{3-7}$cycloalkyl;

$R^3$ is hydrogen or $C_{1-6}$alkyl;

m is 0, 1, 2, or 3;

n is 1 or 2;

X is CO or $SO_2$;

B is selected from $C_{1-6}$alkyl, $C_{3-7}$cycloalkyl, $C_{3-7}$cycloalkylmethyl; $C_{1-3}$methoxyalkyl, and $C_{1-3}$phenoxyalkyl or is selected from phenyl, naphthyl, pyridinyl, pyrimidinyl, pyridazinyl, pyrazinyl, furanyl, thienyl, pyrrolyl, oxazolyl, isoxazolyl, benzfuranyl, benzthienyl, indolyl, benzoxazolyl, and indazolyl moieties that are unsubstituted or substituted with 1 to 2 substituents selected from halo, alkoxy, hydroxy, trifluoromethyl, cyano, and —N($R^3$)$_2$; or a pharmaceutically acceptable salt or solvate.

The term "alkyl" refers to straight or branched chain hydrocarbon groups. The term "alkenyl" refers to straight or branched chain hydrocarbon groups having at least one double bond. The term "alkynyl" refers to straight or branched chain hydrocarbon groups having at least one triple bond. The term "alkylene" refers to bivalent straight or branched chain hydrocarbon groups.

The term "alkoxy" refers to groups such as methoxy, phenyloxy, benzyloxy, and so forth. The term "alkylthio" or "thioalkyl" refers to an alkyl group bonded to a sulfur atom. The term "aminoalkyl" or "alkylamino" refers to an alkyl bonded to an amine nitrogen.

The term "halo" or "halogen" refers to chloro, bromo, fluoro and iodo.

The invention includes all pharmaceutically acceptable salt forms of the instant compounds. Pharmaceutically acceptable salts are those in which the counter ion does not contribute significantly to the pharmacological activity or toxicity of the compound and as such function as pharmacological equivalent. In many instances, the salts have physical properties that make them desirable for formulation, such as solubility or crystallinity. The salts can be made according to common organic techniques using commercially available reagents. Preferred anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Preferred cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the present invention can be isolated as solvated forms, most commonly hydrated forms such as monohydrate, dihydrate, trihydrate, hemihydrate, tetrahydrate and the like. The compounds may also merely retain adventitious solvent or be a mixture of solvate plus some adventitious solvent in some instances. It should be appreciated by those skilled in the art that solvated forms are equivalent to unsolvated forms and are within the scope of the present invention.

As some of the compounds of the present invention can possess chiral carbon atoms, such as the carbons marked with an asterisk in the structures below, the invention includes all forms of the compounds of Formula I as described herein and in the claims. Preferred embodiments of compounds of Formula I include both the racemate or diastereomeric mixture and single enantiomers or diastereomers.

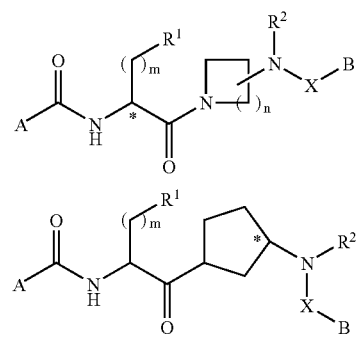

Mixtures of isomers of Formula I compounds or their chiral precursors can be separated into individual isomers according to methods which are commonly known in the art, such as fractional crystallization, chiral HPLC chromatography, or other suitable separation processes. Racemates can also be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the neutral compounds.

One aspect of the invention are compounds of Formula I where A is $C_{1-4}$aminoalkyl, or a heterocycle selected from the group consisting of

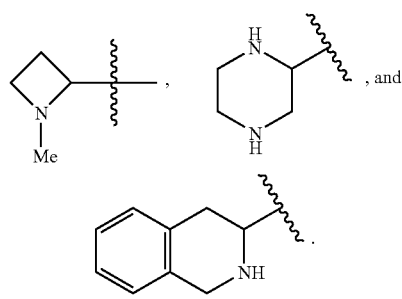

Another aspect of the invention are compounds where m is 1 and $R^1$ is phenyl substituted with 1–2 substituents selected from halo, alkyl, alkyloxy, cyano, and carboalkoxy.

Another aspect of the invention are compounds of Formula I where X is CO and B is selected from $C_{1-6}$alkyl, $C_{3-7}$cycloalkyl, $C_{3-7}$cycloalkylmethyl, $C_{1-3}$methoxyalkyl, and $C_{1-3}$phenoxyalkyl or is selected from phenyl, pyrazinyl, furanyl, isoxazolyl, and benzthienyl, moities that are unsubstituted or substituted with 1 to 2 substituents selected from halo, alkoxy, hydroxy, trifluoromethyl, cyano, and —N($R^3$)$_2$.

Another aspect of the invention are compounds of Formula I where n is 1.

Another aspect of the invention are compounds of Formula I where n is 2.

Another aspect of the invention are compounds of Formula I where the carbon marked with an asterisk, as shown below, is of the (R) stereochemistry.

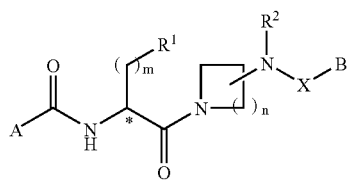

Another aspect of the invention are compounds of Formula I where the carbon marked with an asterisk, as shown below, is of the (S) stereochemistry.

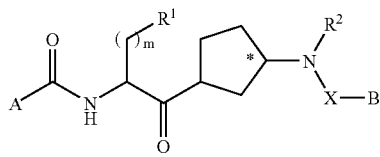

Some compounds of the invention include the following:
N-[1-[(2R)-3-(4-Chlorophenyl)-2-[[3-(dimethylamino)-1-oxopropyl]amino]-1-oxopropyl]-3-azetidinyl]-N-cyclohexyl-3-methyl-butanamide;
(3R)-N-[(1R)-1-[(4-Chlorophenyl)methyl]-2-[3-[cyclohexyl(5-isoxazolylcarbonyl)amino]-1-pyrrolidinyl]-2-oxoethyl]-1,2,3,4-tetrahydro-3-isoquinolinecarboxamide;
(3R)-N-[(1R)-1-[(4-Chlorophenyl)methyl]-2-[(3S)-3-[cyclohexyl(5-isoxazolylcarbonyl)amino]-1-pyrrolidinyl]-2-oxoethyl]-1,2,3,4-tetrahydro-3-isoquinolinecarboxamide;
(2S)-N-[(1R)-1-[(4-Chlorophenyl)methyl]-2-[(3S)-3-[cyclohexyl(1-oxopentyl)amino]-1-pyrrolidinyl]-2-oxoethyl]-1,2,3,4-tetrahydro-3-isoquinolinecarboxamide;
(3R)-N-[(1R)-1-[(4-Chlorophenyl)methyl]-2-[(3S)-3-[cyclohexyl(2-furanylcarbonyl)amino]-1-pyrrolidinyl]-2-oxoethyl]-1,2,3,4-tetrahydro-3-isoquinolinecarboxamide;
N-[1-[(2R)-3-(4-Chlorophenyl)-2-[(3S)-[3-(dimethylamino)-1-oxopropyl]amino]-1-oxopropyl]-3-pyrrolidinyl]-N-cyclohexyl-3-methyl-butanamide; and
(3R)-N-[(1R)-1-[(4-Chlorophenyl)methyl]-2-[(3S)-3-[cyclohexyl(methylsulfonyl)amino]-1-pyrrolidinyl]-2-oxoethyl]-1,2,3,4-tetrahydro-3-isoquinolinecarboxamide.

Synthetic Methods

The compounds of Formula I were prepared using general routes as illustrated below in Schemes 1–3. In Scheme 1, amino alcohol 2 can be mesylated with MsCl and the resulting mesylate intermediate (not shown) can be reacted with an appropriate amine to furnish the benzhydryl protected diamine 3. The benzhydryl group can be removed by hydrogenolysis using Pearlman's catalyst to give diamine 4. Diamine 4 can be condensed with amino acid 5 with diethylphosphorylbenzotriazolone (DEPBT) to afford amino amide 6. Final condensation with either acyl or sulfonyl chloride under conventional conditions can then provide compounds of Formula I.

Scheme 1

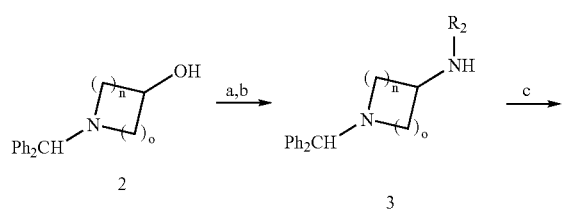

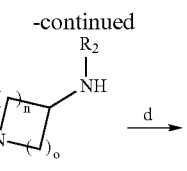

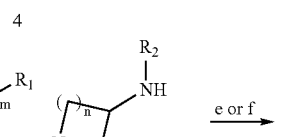

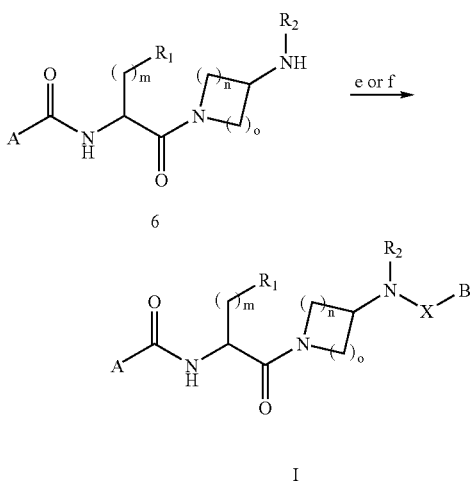

Amino amide 5 used above in Scheme 1 can be prepared by condensation of an appropriate amino acid with the functionalized acid $ACO_2H$ via standard peptide coupling methods.

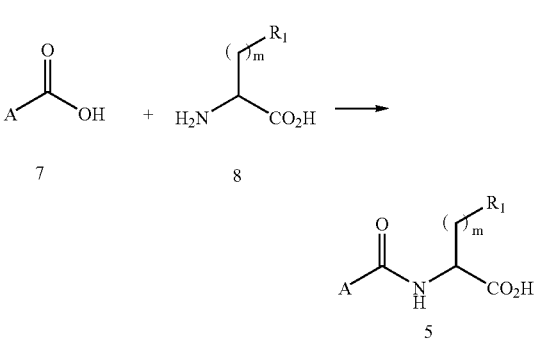

An alternative route to Formula I compounds is shown in Scheme 2. Diamine 4 can be coupled with an N-t-butyloxycarbonyl (BOC or Boc) amino acid 9 to give amino amide 10 which can subsequently be condensed with an acyl chloride and then deprotected under acidic conditions to furnish 11. Treatment of 11 with $ACO_2H$ (7) can then provide compounds of Formula I. Alternatively, compounds of Formula I can be prepared from 10 by a deprotection/coupling sequence with $ACO_2H$ (7) to give 6 followed by a final condensation with an acyl chloride.

In another example, Formula I compounds can be prepared using the Scheme 2 procedure described below. Intermediate aminoamide 10 can be deprotected using HCl in dioxane and MeOH and the resulting amino amide acylated with $ACO_2H$ (7) as described above to give compound 6. These can be further acylated or sulfonated in a manner similar to that described above in Scheme 1 to give compounds of Formula I.

Scheme 2

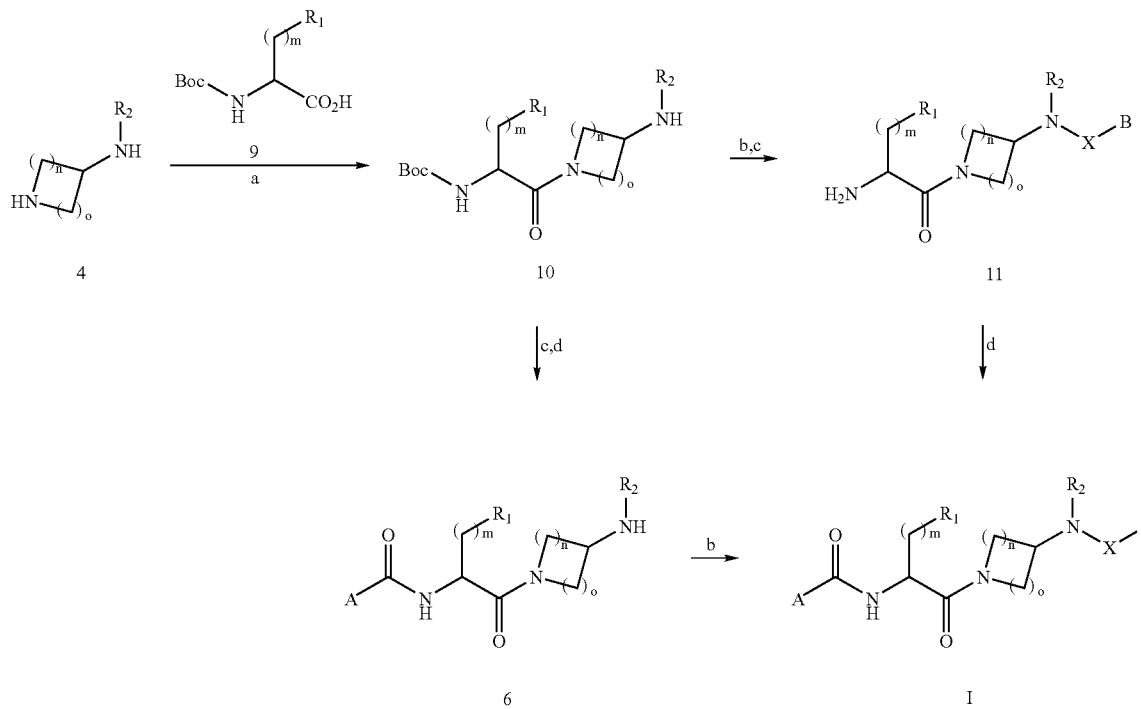

In another example, Formula I compounds can be prepared according to the routes outlined below in Scheme 3. Amine 12 can be treated with benzyl chloroformate to give the benzyloxycarbonyl (CBZ) protected derivative 13. These can then subsequently de-Boced by treatment with HCl in dioxane/$CH_2Cl_2$ to give the CBZ-amine 14. Reductive amination of 14 with the appropriate aldehyde or ketone using $NaBH_3CN$ can furnish the alkylated amine 15, which after hydrogenolysis over 10% Pd/C can yield diamine 4. Condensation of 4 with the appropriate Boced amino acid 7 under standard peptide coupling procedures can give the intermediate amino amide 10. These intermediates can be in turn either acylated or sulfonated with the appropriate acid or sulfonyl chloride to afford 16 and then de-Boced in a manner similar to that described for 14 above to give the penultimate amino amide 11. Compounds of Formula I can then be prepared by treatment of amino amide 11 with the appropriate acid derivative 7 in a manner similar to that described in Scheme 2.

Scheme 3

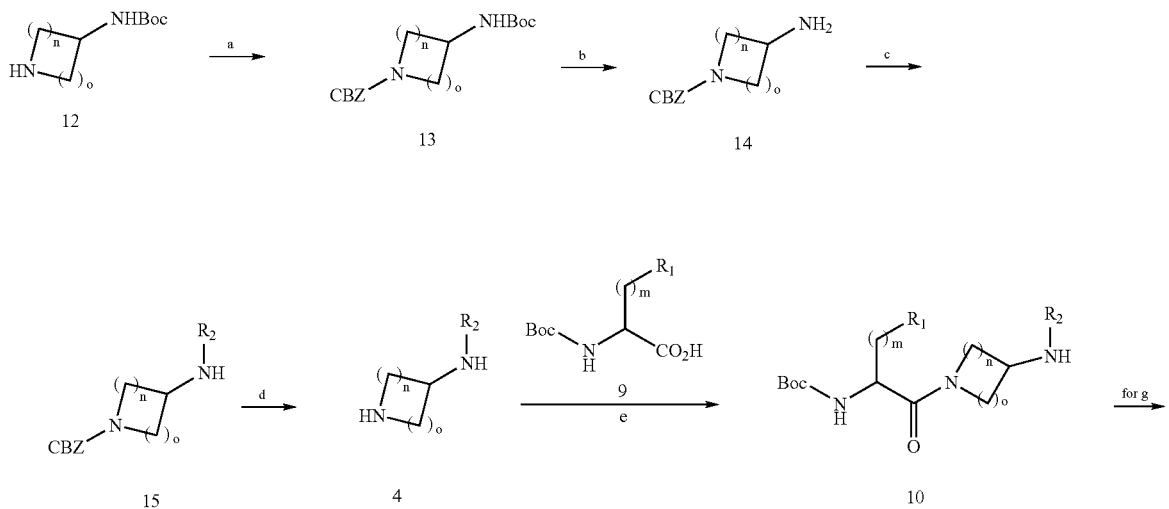

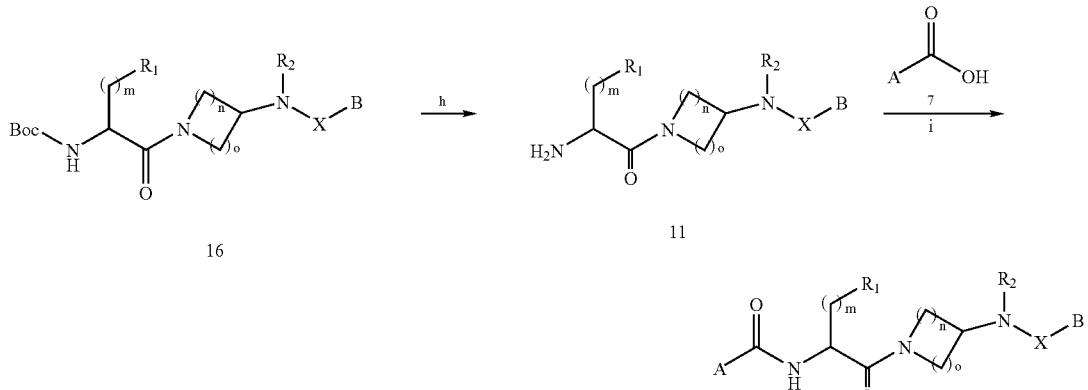

[a] PhCH2OCOCl, Et3N, CH2Cl2. [b] HCl, dioxane, CH2Cl2. [c] aldehyde or ketone, NaBH3CN, MeOH.
[d] H2, Pd/C, 6N HCl (aq), EtOH. [e] 9, ClCO3Et, Et3N, CH2Cl2. [f] Acyl chloride, Et3N, CH2Cl2.
[g] Sulfonyl chloride, Et3N, CH2Cl2. [h] HCl, dioxane. [i] ACO2H (7), DEPBT, Et3N, CH2Cl2.

Biological Methods

Melanocortin MC4R Binding Assay. The compounds of this invention demonstrate melanocortin binding affinity. A membrane binding assay was used to identify competitive ligands of [$^{125}$I]NDP-α-MSH binding to cloned human MC4R receptors expressed in Hi5 insect cells or HEK-293 cells transfected by a baculovirus/human MC4R receptor construct. The membrane binding buffer was composed of 25 mM HEPES, pH 7.4, 140 mM NaCl, 1.2 mM $MgCl_2$, 2.5 mM $CaCl_2$, and 0.1% BSA Membrane protein (0.5 μg) and [$^{125}$I]-NDP-α-MSH (to a final concentration of 0.1 nM) were added. Competing ligands or a buffer blank were added and incubated for 90 minutes at 37° C. After filtration, the cell membranes were evaluated in a Wallac Microbeta Trilux Scintillation and Luminescence Counter (Model 1450). Dose-response cureves were fitted by linear regression analyses and $IC_{50}$ values are calculated using ExcelFit. Binding data is shown in Table 1. MC4R $IC_{50}$ values: <250 nM=+++; 250–1000 nM=++; 1000–10000=+.

TABLE 1

| Example | MC4R $IC_{50}$ (nM) |
|---|---|
| 1 | ++ |
| 2 | +++ |
| 3 | ++ |
| 4 | ++ |
| 5 | ++ |
| 6 | + |
| 7 | ++ |
| 8 | ++ |
| 9 | ++ |
| 10 | ++ |
| 11 | ++ |
| 12 | ++ |
| 13 | + |
| 14 | +++ |
| 15 | ++ |
| 16 | +++ |
| 17 | +++ |
| 18 | +++ |

TABLE 1-continued

| Example | MC4R $IC_{50}$ (nM) |
|---|---|
| 19 | ++ |
| 20 | +++ |
| 21 | +++ |
| 22 | +++ |
| 23 | + |
| 24 | + |
| 25 | ++ |
| 26 | +++ |
| 27 | +++ |
| 28 | ++ |
| 29 | +++ |
| 30 | +++ |
| 31 | ++ |
| 32 | +++ |
| 33 | +++ |
| 34 | +++ |
| 35 | +++ |
| 36 | + |
| 37 | + |
| 38 | ++ |
| 39 | ++ |
| 40 | ++ |
| 41 | + |
| 42 | ++ |
| 43 | + |
| 44 | + |
| 45 | +++ |
| 46 | +++ |
| 47 | + |
| 48 | + |
| 49 | + |
| 50 | + |
| 51 | ++ |
| 52 | + |
| 53 | + |
| 54 | ++ |
| 55 | + |
| 56 | + |
| 57 | + |
| 58 | + |
| 59 | + |
| 60 | +++ |
| 61 | + |

TABLE 1-continued

| Example | MC4R IC$_{50}$ (nM) |
|---|---|
| 62 | + |
| 63 | + |
| 64 | ++ |
| 65 | + |
| 66 | + |
| 67 | +++ |
| 68 | ++ |
| 69 | +++ |

MC4R IC$_{50}$ values: <250 nM = +++; 250–1000 nM = ++; 1000–10000 nM = +.

Pharmaceutical Composition and Methods of Treatment

The compounds of this invention bind to MC-4R receptors. The modulation of melanocotin receptor has been demonstrated to affect a variety of physiological processes such as obesity, fluid retention, thermoregulation, and penile erection. Thus, the compounds of this invention can provide beneficial therapeutic treatment for such conditions as obesity and sexual dysfunction.

The compounds of this invention are generally given as pharmaceutical compositions comprised of a therapeuticall effective amount of a compound of Formula I or its pharmaceutically acceptable salt and a pharmaceutically acceptable carrier and may contain conventional exipients. A therepeutically effective amount is that which is needed to provide a meaningful patient benfit. Pharmaceutically acceptable carriers are those conventionally known carriers having acceptable safety profiles. Compositions encompass all common forms including as capsules, tablets, losenges, and powders as well as liquid suspensions, syrups, elixers, and solutions. The compositions are made using common formulation techniques. Conventional excipients (such as binding and wetting agents) and vehicles (such as water and alcohols) may be used for the composition. The compostions are generally formulated in dosage units and compositions providing from about 1 to 1000 mg of the active ingredient per dose are preferred.

The method of treatment involves administering a therapeutically effective amount of a Formula I compound or a pharmaceutically acceptable salt to a patient exhibiting conditions responsive to MC4R receptor modulation. The method includes all conventional modes of administration. Typical modes are oral, topical, rectal, nasal, and parenteral. Generally the daily dosage will be from about 0.001 mg to 100 mg of Formula I compound per kilogram of bodyweight when used for obesity, diabetes, or sexual dysfunction. The specific dosing regimen, however, must be carefully adjusted using sound medical judgement.

DESCRIPTION OF SPECIFIC EMBODIMENTS

Intermediate 3

N-diphenylmethyl-N'-cyclohexyl-3-aminoazetidine. To a suspension of the commercially available HCl salt of N-diphenylmethyl-3-hydroxazetidine (3.31 mmol, 1.0 equiv) in CH$_2$Cl$_2$ (20 mL) was added Et$_3$N (1.15 mL, 2.5 equiv.). After dissolution of the amine, methanesulfonyl chloride (0.513 mL, 3.97 mmol) was added and the resulting solution was stirred at ambient temperatures for 1 h. The solution was then partitioned between an aqueous sat. NaHCO$_3$ solution and CH$_2$Cl$_2$. The layers were separated and the aqueous layer was extracted with CH$_2$Cl$_2$. The combined organic portions were washed with water, brine, dried over Na$_2$SO$_4$, and concentrated in vacuo to furnish the mesylate as a light yellow oil which gradually solidified on standing. The crude mesylate (280 mg, 1.0 equiv) was mixed with cycloalkylamine (5.0 equiv) and toluene (3.0 mL) in a microwavable tube and heated at 160° C. for 45 min under microwave irradiation. The resulting mixture was directly purified by flash column chromatography to afford the product in 42% yield isolated as a clear oil: MS Calcd for C$_{22}$H$_{28}$N$_2$ [M+H]: 321. Found: 321.

Intermediate 4

Prepared as in Scheme 1. Intermediate 3 was dissolved in Et$_2$O and made acidic with 1 N ethereal HCl to yield, after filtration, the bis-HCl salt as white solid. The salt was dissolved in 25 mL of MeOH/EtOH (1:1) and 50 mg of Pearlman's catalyst (20% Pd(OH)$_2$ on carbon) added. The resulting mixture was shaken on a Parr hydrogenation apparatus under H$_2$ (55 psi) for 20 h and then filtered and concentrated in vacuo to give Intermediate 4 as a white solid, which was directly carried on to the next reaction.

Prepared as in Scheme 3. (3S)-cyclohexyl-pyrrolidin-3-yl-amine, dihydrochloride. To a solution of (3S)-3-cyclohexylamino-pyrrolidine-1-carboxylic acid benzyl ester (4.24 g, 14 mmol) in ethanol (100 mL) under nitrogen was added 10% Palladium on carbon (100 mg) followed by 6 N aqueous hydrogen chloride (4.67 mL, 28 mmol). The reaction mixture was then brought under hydrogen (1 atmosphere) and stirring continued for additional 12 h. The catalyst was then filtered and the solvent was evaporated to give (3S)-cyclohexyl-pyrrolidin-3-yl-amine, dihydrochloride as a foam in quantitative yield. $^1$H NMR (300 MHz, CD$_3$OD): in δ 4.35–4.20 (m, 1H), 3.86–3.75 (m, 1H), 3.71–3.49 (m, 2H), 3.50–3.36 (m, 1H), 3.30–3.17 (m, 1H), 2.70–2.55 (m, 1H), 2.45–2.30 (m, 1H), 2.28–2.12 (m, 2H), 1.86–1.20 (m, 8H); MS (ESI+), 169 (M+H); R$_f$=1.59.

Intermediate 6

Intermediate 4 (0.2 mmol, 1.0 equiv.) was suspended in 2 mL of CH$_2$Cl$_2$ and Et$_3$N was added dropwise to dissolve all of the solid. To the resulting clear solution was added aminoacid 5 (1.1 equiv). Excess Et$_3$N was added to dissolve the solid and the coupling reagent DEPBT (82 mg, 1.3 equiv) was added in one portion. The reaction mixture was stirred for 15 h and then partitioned between 1 N NaOH and CH$_2$Cl$_2$. The layers were separated and the aqueous layer extracted with CH$_2$Cl$_2$. The combined organic portions were dried (Na$_2$SO$_4$) and concentrated in vacuo to give Intermediate 6.

The following representative compounds were prepared by this method:

N-[1-(4-chloro-benzyl)-2-(3-cyclopentylamino-azetidin-1-yl)-2-oxo-ethyl]-3-dimethylamino-propionamide. MS Calcd for C$_{22}$H33ClN$_4$O$_2$ [M+H]: 421. Found: 421;

N-[1-(4-chloro-benzyl)-2-(3-cyclohentylamino-azetidin-1-yl)-2-oxo-ethyl]-3-dimethylamino-propionamide. MS Calcd for $C_{23}H_{35}ClN_4O_2$ [M+H]: 435. Found: 435;

N-[1-(4-chloro-benzyl)-2-(3-cycloheptylamino-azetidin-1-yl)-2-oxo-ethyl]-3-dimethylamino-propionamide. MS Calcd for $C_{24}H_{37}ClN_4O_2$ [M+H]: 449. Found: 449.

Intermediate 10

Isoxazole-5-carboxylic acid {1-[2-(t-butyloxycarbonyl)-amino-3-(4-chloro-phenyl)-propionyl]-azetidin-3-yl}-cyclohexyl-amide. Prepared as in Scheme 1, Intermediate 4 was coupled to N-Boced amino acid 9 using DEPBT and Et$_3$N in CH$_2$Cl$_2$ to give Intermediate 10. As an example of this procedure, isoxazole-5-carboxylic acid {1-[2-(t-butyloxycarbonyl)-amino-3-(4-chloro-phenyl)-propionyl]-azetidin-3-yl}-cyclohexyl-amide was isolated in 65% yield as a tan oil: MS Calcd for $C_{23}H_{34}ClN_3O_3$ [M+H], 436. Found, 436.

(1R)-[1-(4-chloro-benzyl)-2-{(3S)-3-cyclohexylamino-pyrrolidin-1-yl}-2-oxo-ethyl]-carbamic acid tert-butyl ester. Prepared as in Scheme 3. To a well stirred solution of (2R)-2-tert-butoxycarbonylamino-3-(4-chloro-phenyl)-propionic acid (5.0 g, 16.8 mmol) in dichloromethane (150 mL) at –20° C. was added ethyl chloroformate (1.6 mL, 16.5 mmol) followed by triethylamine (2.4 mL, 17 mmol). After 20 min 3b. 2HCl (3.4 g, 14 mmol) in dichloromethane (20 mL) containing triethylamine (3.9 mL, 28 mmol) was added to the reaction mixture. After 3 h, the reaction mixture was washed with aqueous sodium bicarbonate (60 mL), brine (50 mL) and dried (Na$_2$SO$_4$). The crude product was purified by flash chromatography using 5% methanol in dichloromethane to give (1R)-[1-(4-chloro-benzyl)-2-{(3S)-3-cyclohexylamino-pyrrolidin-1-yl}-2-oxo-ethyl]-carbamic acid tert-butyl ester in 89% yield. $^1$H NMR (300 MHz, CDCl$_3$): in δ 7.20–7.16 (m, 2H), 7.10–7.06 (m, 2H), 5.45–5.35 (m, 1H), 4.56–4.38 (m, 1H), 3.65–3.46 (m, 1H), 3.41–3.26(m, 1H), 3.20–3.08 (m, 1H), 3.00–2.75 (m, 4H), 2.40–2.15 (m, 2H), 1.95–0.85 (m, 10H), 1.36 (s, 9H); $^{13}$C NMR (300 MHz, CDCl$_3$): in δ 169.8, 155.0, 135.2, 132.8, 130.8, 128.5, 128.4, 79.7, 54.7, 53.0, 52.7, 52.1, 44.7, 44.0, 43.4, 39.5, 34.1, 33.6, 32.4, 31.0, 28.5, 25.9, 25.0; MS (ESI+), 450 (M+H); R$_f$=1.48.

Intermediate 11

Isoxazole-5-carboxylic acid {1-[2-amino-3-(4-chloro-phenyl)-propionyl]-azetidin-3-yl}-cyclohexyl-amide. {1-[2-Amino-3-(4-chloro-phenyl)-propionyl]-azetidin-3-yl}-cyclohexylamine was acylated with isoxazole-5-carbonyl chloride in a manner similar to that described for 6 above and then the Boc protecting group removed by treatment with a solution of HCl in dioxane and MeOH to furnish isoxazole-5-carboxylic acid {1-[2-amino-3-(4-chloro-phenyl)-propionyl]-azetidin-3-yl}-cyclohexyl-amide. $^1$H NMR (400 MHz, CDCl$_3$) δ 8.33–8.29 (m, 1H), 7.32–7.12 (m, 4H), 6.77–6.71 (m, 1H), 4.54 (br, 2H), 4.34–3.80 (m, 2H), 3.60–3.40 (m, 2H), 3.20–2.70 (m, 2H), 2.60–2.05 (m, 2H), 1.86–1.60 (m, 4H), 1.60–1.00 (m, 4H), 0.90–0.78 (m, 3H); MS Calcd for $C_{22}H_{27}ClN_4O_3$ [M+H], 431. Found, 431.

Prepared according to Scheme 3. To a stirred solution Boced amino amide intermediate 16 (1 mmol) in dichloromethane (5 mL) was added a saturated solution of hydrogen chloride in dioxane (10 mL) at room temperature. After 2 h, the solvent was evaporated to give the following representative amine hydrochlorides 11 in quantitative yields:

Furan-2-carboxylic acid {(2R)-1-[2-amino-3-(4-chloro-phenyl)-propionyl]-(3S)-pyrrolidin-3-yl}-cyclohexyl-amide, hydrochloride. $^1$H NMR (300 MHz, CDCl$_3$): in δ 7.67–7.65 (m 1H), 7.43–7.29 (m, 4H), 6.94–6.88 (m, 1H), 6.59–6.58 (m, 1H), 4.43–4.12 (m, 2H), 3.90–3.40 (m, 4H), 3.40–3.00 (m, 4H), 2.70–1.20 (m, 10H); $^{13}$C NMR (300 MHz, CDCl$_3$): in δ 167.7, 162.8, 145.8, 134.3, 132.6, 130.3, 116.5, 112.5, 68.2, 60.2, 55.5, 53.7, 46.2, 37.9, 32.8, 30.3, 28.0, 26.9, 26.2; MS (ESI+), 444 (M+H); R$_f$=1.53.

N-{1-[(2R)-2-Amino-3-(4-chloro-phenyl)-propionyl]-(3S)-pyrrolidin-3-yl}-N-cyclohexyl-isobutyramide hydochloride. $^1$H NMR (500 MHz, CDCl$_3$): in δ 7.41–7.32 (m, 4H), 4.40–4.28 (m, 1H), 3.80–3.55 (m, 3H), 3.40–3.15 (m, 4H), 3.05–3.00 (m, 1H), 2.90–2.75 (m, 1H), 2.55–2.45 (m, 1H), 2.35–2.23 (m, 1H), 1.95–1.16 (m, 12H), 1.14 (m, 6H); MS (ESI+), 420 (M+H); R$_f$=1.71.

N-{1-[(2R)-2-Amino-3-(4-chloro-phenyl)-propionyl]-(3S)-pyrrolidin-3-yl}-N-cyclohexyl-benzenesulfonamide hyrochloride. $^1$H NMR (500 MHz, MeOH, D4): in δ 7.85–7.80 (m, 2H), 7.63–7.56 (m, 3H), 7.42–7.40 (m, 2H), 7.30–7.27 (m, 2H), 4.30–4.38 (m, 1H), 4.1–2.95 (m, 8H), 2.74–2.70 (m, 1H), 2.52–2.41 (m, 1H), 2.1–1.05 (m, 10H); MS (ESI+), 492 (M+2H); R$_f$=1.43.

Intermediate 13

(3-S)-3-tert-butoxcarbonylamino-pyrrolidine-1-carboxylic acid, benzyl ester. To a well stirred solution of (3S)-3-(tert-butoxycarbonylamino)pyrrolidine (12b, 5 g, 27 mmol) in dichloromethane (150 mL) at 0° C. was added triethylamine (4.2 mL, 30 mmol) followed by slow addition of benzyl chloroformate (4.28 mL, 30 mmol). The reaction mixture was stirred for additional 2 h followed by treatment with aqueous sodium bicarbonate (100 mL), brine (50 mL) to give (3-S)-3-tert-butoxycarbonylamino-pyrrolidine-1-carboxylic acid, benzyl ester in 98% yield. The compound was crystallized from 30% ethyl acetate in hexane as a white crystalline solid. $^1$H NMR (300 MHz, CDCl$_3$): in δ 7.36–7.25 (m, 5H), 5.12 (s, 2H), 4.72–4.6 (m, 1H), 4.24–4.11 (m, 1H), 3.7–3.6 (m, 1H), 3.55–3.38 (m, 2H), 3.3–3.15 (m, 1H), 2.2–2.16 (m, 1H), 1.9–1.7 (m, 1H), 1.43 (s, 9H); MS (ESI+), 321 (M+H); R$_f$=1.53.

Intermediate 14

(3S)-3-amino-pyrrolidine-1-carboxylic acid, benzyl ester. To a solution of (3-S)-3-tert-butoxcarbonylamino-pyrrolidine-1-carboxylic acid, benzyl ester (8 g, 25 mmol) in dichloromethane (50 mL) was added a saturated solution of hydrogen chloride in dioxane (50 mL) at room temperature. After 2 h, the solvent was evaporated and the crude reaction mixture was diluted with dichloromethane (300 mL) followed by treatment with aquous sodium bicarbonate (200 mL), brine (50 mL) and dried (Na$_2$SO$_4$). The solvent was evaporated to give benzyl ester (3S)-3-amino-pyrrolidine-1-carboxylic acid, benzyl ester in quantitative yield. $^1$H NMR (300 MHz, CDCl$_3$): in δ 7.35–7.25 (m, 5H), 5.11 (s, 2H), 3.68–3.44 (m, 5H), 3.18–3.10 (m, 1H), 2.05–2.03 (m, 1H), 1.80–1.69 (m, 1H); MS (ESI+), 221 (M+H); R$_f$=0.88.

Intermediate 15

(3S)-3-cyclohexylamino-pyrrolidine-1-carboxylic acid benzyl ester. To a stirred solution of (3S)-3-amino-pyrrolidine-1-carboxylic acid, benzyl ester (4.40 g, 20 mmol) in methanol (120 mL) was added cyclohexanone (2.75 g, 28 mmol) followed by sodium cyanoborohydride (1.50 g, 24 mmol) at room temprerature. After 3 h, the reaction mixture was concentrated, diluted with dichloromethane (200 mL), washed with aqueous sodium bicarbonate (100 mL), 1 N sodium hydroxide (50 mL), brine (50 mL) and dried ($Na_2SO_4$). The crude was purified by flash chromatography using 5% methanol in dichloromethane to give (3S)-3-cyclohexylamino-pyrrolidine-1-carboxylic acid benzyl ester in 73% yield. $^1H$ NMR (300 MHz, $CDCl_3$): in δ 7.36–7.26 (m, 5H), 5.11 (s, 2H), 3.65–3.35 (m, 4H), 3.1–2.95 (m, 1H), 2.5–2.38 (m, 1H), 2.11–1.98 (m, 1H), 1.92–1.54 (m, 5H), 1.31–0.95 (m, 6H); $^{13}C$ NMR (300 MHz, $CDCl_3$): in δ 154.9, 137.1, 128.4, 127.8, 66.7, 55.0, 54.6, 53.8, 52.6, 44.7, 44.3, 34.1, 32.8, 32.0, 26.1, 25.1; MS (ESI+), 303 (M+H); $R_f$=1.16.

Intermediate 16

To a well stirred solution of (1R)-[1-(4-chloro-benzyl)-2-{(3S)-3-cyclohexylamino-pyrrolidin-1-yl}-2-oxo-ethyl]-carbamic acid tert-butyl ester (0.9 g, 2 mmol) in dichloromethane (20 mL) was added triethylamine (0.56 mL, 4 mmol) followed by the appropriate acid or sulfonyl chloride (3 mmol) at room temperature. After 4 h, the reaction mixture was diluted with dichloromethane (50 mL) followed by washing with aqueous sodium bicarbonate solution (40 mL), brine (30 mL) and dried ($Na_2SO_4$). The crude products were purified either by flash chromatography ($SiO_2$: EtOAc/hexanes) or preparative HPLC (Xterra 30×100 mm, MeOH, $H_2O$, TFA) to give the desired products shown below.

(1R)-(1-(4-Chloro-benzyl)-2-{(3S)-3-[cyclohexyl-(furan-2-carbonyl)-amino]-pyrrolidin-1-yl}-2-oxo-ethyl)-carbamic acid, tert-butyl ester. $^1H$ NMR (300 MHz, $CDCl_3$): in δ 7.47–7.46 (m, 1H), 7.29–7.13 (m, 4H), 6.89–6.83 (m, 1H), 6.47–6.44 (m, 1H), 5.50–5.35 (m, 1H), 4.66–4.48 (m, 1H), 4.00–3.60 (m, 4H), 5.59–3.46 (m, 1H), 3.35–3.25 (m, 1H), 3.06–2.95 (m, 1H), 2.90–2.80 (m, 1H), 2.70–2.50 (m, 1H), 2.10–0.95 (m, 10H); $^{13}C$ NMR (300 MHz, $CDCl_3$): in δ 169.6, 160.7, 148.7, 143.6, 135.4, 132.8, 131.1, 128.5, 115.5, 111.3, 58.4, 53.4, 44.3, 40.0, 31.7, 29.3, 28.3, 25.8, 25.2, 24.9; MS (ESI+), 544 (M+H); $R_f$=1.86.

(1R)-{1-(4-Chloro-benzyl)-2-[(3S)-3-(cyclohexyl-isobutyryl-amino)-pyrrolidin-1-yl]-2-oxo-ethyl}-carbamic acid, tert-butyl ester. $^1H$ NMR (500 MHz, $CDCl_3$): in δ 7.26–7.23 (m, 2 H), 7.19–7.12 (m, 2H), 4.60–4.40 (m, 1H), 3.75–3.28 (m, 4H), 3.07–3.00 (m, 1H), 2.88–2.80 (m, 1H), 2.75–2.38 (m, 3H), 1.95–1.54 (m, 6H), 1.46–1.06 (m, 11H), 1.38 (s, 9H); MS (ESI+), 520 (M+H); $R_f$=1.99.

[2-[(3S)-3-(Benzenesulfonyl-cyclohexyl-amino)-pyrrolidin-1-yl]-(1R)-(4-chloro-benzyl)-2-oxo-ethyl]-carbamic acid, tert-butyl ester. $^1H$ NMR (500 MHz, $CDCl_3$): δ 7.82–7.77 (m, 2H), 7.56–7.49 (m, 3H), 7.33–7.31 (m, 2H), 7.16–7.15 (m, 2H), 5.87–5.63 (m,1H), 4.56–4.54 (m, 1H), 3.92–2.94 (m, 7H), 2.52–2.40(m, 1H), 2.28–2.18 (m, 1H), 1.98–1.05 (m, 19H), MS (ESI+), 592 (M+2H); $R_f$=1.69.

EXAMPLES

General procedure for preparing Formula I compounds from Intermediate 6. To a solution of Intermediate 6 (1.0 equiv) dissolved in $CH_2Cl_2$ was added $Et_3N$ (2.0 equiv) followed by addition of the individual acyl or sulfonyl chloride (1.1 equiv). The resulting mixture was stirred at ambient temperature for 4 h and then partitioned between 1 N NaOH and $CH_2Cl_2$. The layers were separated and the aqueous layer was extracted with $CH_2Cl_2$. The combined organic extracts were washed with water, brine, dried ($Na_2SO_4$) and concentrated in vacuo. The final products were generally analyzed by high pressure liquid chromatography/mass spec [(LC/MS), Xterra 3.0×50 mm S7 column, 2 min gradient elution @ 5 mL/min starting with 10:90:0.1 $MeOH:H_2O:TFA$ and ending with 90:10:0.1 aforementioned mixture] and purified by by preparative high pressure liquid chromatography [(HPLC)., Xterra 30×100 mm S7, 8 min gradient elution @ 40 ml/min starting at 30:70:.01 MeOH:$H_2O$:TFA an ending at 100:0.1 MeOH:TFA]. In some instances, the products were purified by either flash chromatography or preparative thin layer (TLC) chromatography and further characterized by $^1H$ NMR analysis in the indicated solvent.

General Procedure for the preparation of Formula I compounds from Intermediate 11 (Procedure A). To a solution of the appropriate Boced amino acid (7, 0.2 mmol) in dichloromethane (6 mL) at 0° C. was added 4-methylmorpholine (21 mg, 0.2 mmol) followed by ethyl chloroformate (22 mg, 0.2 mmol). After 20 min, a solution of 11. HCl (0.1 mmol) in dichloromethane (5 mL) containing 4-methylmorpholine (11 mg, 0.1 mmol was added and stirring continued an additional 2 h. The reaction mixture was then washed with aqueous sodium bicarbonate (5 mL), brine (5 mL) and dried ($Na_2SO_4$). The crude product was purified by flash chromatography using 3% methanol in dichloromethane to give the intermediate Boced amino amide. For example, (1R)-[2-(1-(4-chloro-benzyl)-2-{(3S)-3-[cyclohexyl-(furan-2-carbonyl)-amino]-pyrrolidin-1-yl}-2-oxo-ethylcarbamoyl)-ethyl]-carbamic acid, tert-butyl ester was isolated as a white solid in 84% yield. $^1H$ NMR (300 MHz, $CDCl_3$): in δ 7.46–7.42 (m, 1H), 7.28–7.11 (m, 4H), 6.86–6.82 (m, 1H), 6.44–6.42 (m, 1H), 5.15–4.85 (m, 2H), 3.82–3.50 (m, 4H), 3.35–3.26 (m, 3H), 3.05–2.85 (m, 2H), 2.76–3.28 (m, 4H), 1.86–1.05 (m, 10H); MS (ESI+), 615 (M+H); $R_f$=1.82.

These Boced amino amide intermediates were then deprotected using the following procedure. To a solution of (0.08 mmol) of the Boced amino amide in dichloromethane (4 mL) was added a saturated solution of hydrogen chloride in dioxane (6 mL) at room temperature. After 2 h, the solvent was evaporated to give compounds of Formula I.

General Procedure for the preparation of Formula I compounds from Intermediate 11 (Procedure B). To a solution of the appropriate amino acid HCl salt (7, 0.2 mmol) in dichloromethane (6 mL) at −40° C., was added 4-methylmorpholine (40 mg, 0.4 mmol) followed by ethyl chloroformate (22 mg, 0.2 mmol). After 15 min, a solution 11HCl (0.1 mmol) in dichloromethane (2 mL) containing 4-methylmorpholine (11 mg, 0.1 mmol) was added. After 1 h, the reaction mixture was concentrated and the crude product was purified by preparative HPLC.

The following examples were made using the methods described above.

TABLE 2

| Example Number | Structure | Isolated Yield | MS (ESI) | $t_R$ (min) |
|---|---|---|---|---|
| 1 | 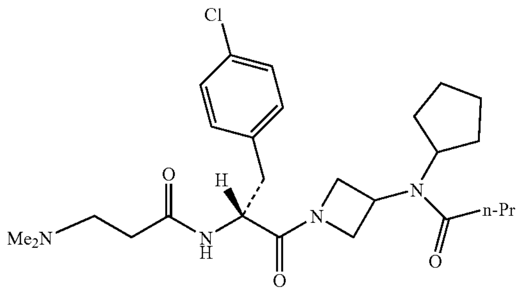 | 7% | 491 | 1.53 |
| 2 | 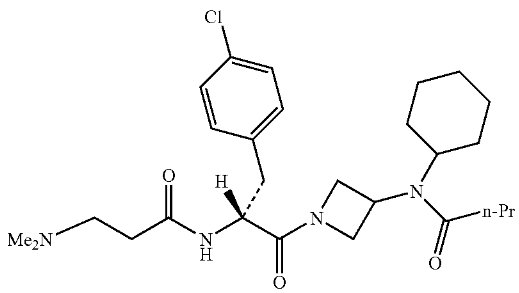 | 27% | 505 | 1.66 |
| 3 | 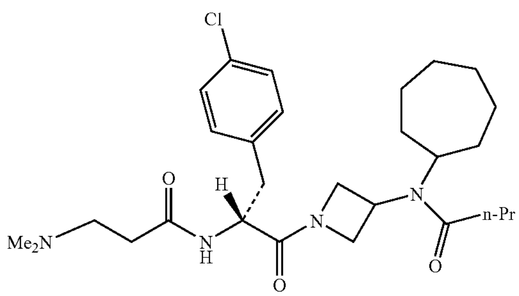 | 9% | 519 | 1.71 |
| 4 | 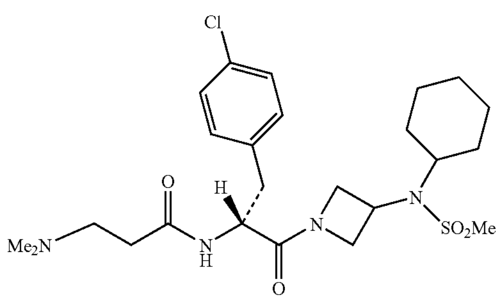 | 23% | 513 | 1.43 |
| 5 | 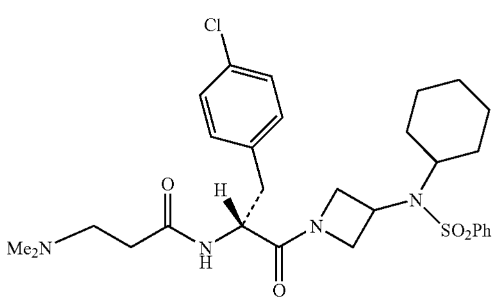 | 15% | 575 | 1.65 |

TABLE 2-continued

| Example Number | Structure | Isolated Yield | MS (ESI) | $t_R$ (min) |
|---|---|---|---|---|
| 6 | (structure) | 42% | 530 | 1.45 |
| 7 | (structure) | 23% | 517 | 1.69 |
| 8 | (structure) | 36% | 545 | 1.83 |
| 9 | (structure) | 31% | 533 | 1.79 |
| 10 | (structure) | 45% | 553 | 1.70 |

TABLE 2-continued

| Example Number | Structure | Isolated Yield | MS (ESI) | $t_R$ (min) |
|---|---|---|---|---|
| 11 | 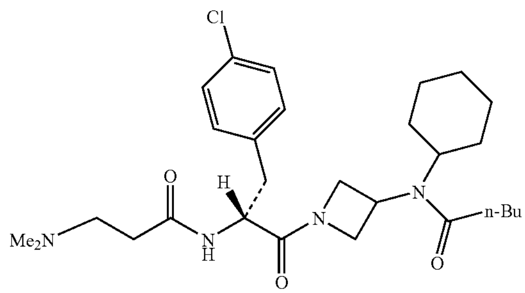 | 48& | 519 | 1.73 |
| 12 | 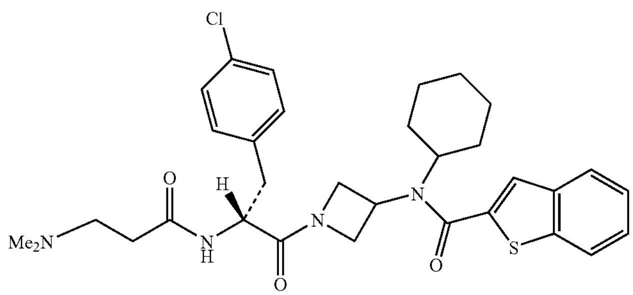 | 18% | 595 | 1.83 |
| 13 | 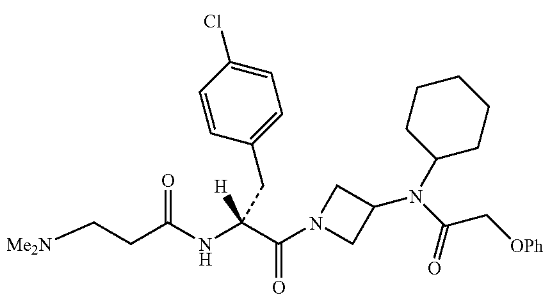 | 34% | 569 | 1.70 |
| 14 | 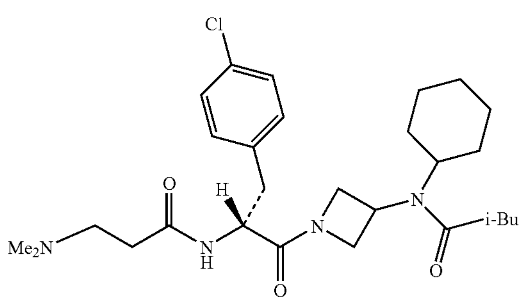 | 21% | 519 | 1.71 |
| 15 | 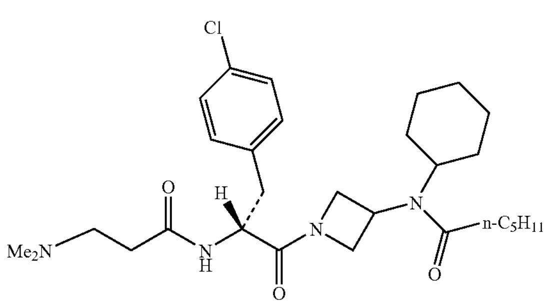 | 27% | 533 | 1.82 |

TABLE 2-continued
| Example Number | Structure | Isolated Yield | MS (ESI) | $t_R$ (min) |
|---|---|---|---|---|
| 16 | 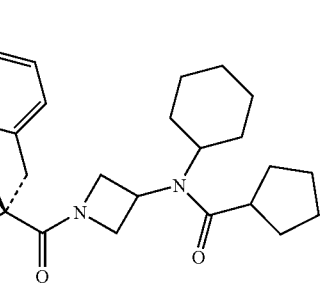 | 10% | 531 | 1.77 |
| 17 | 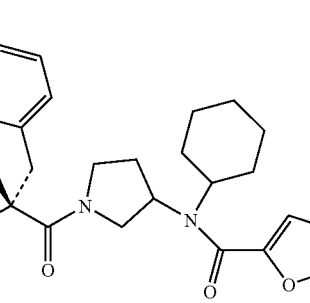 | 61% | 604 | 1.56 |
| 18 | 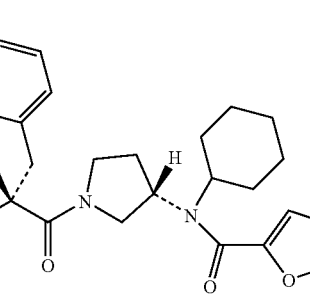 | 41% | 604 | 1.60 |
| 19 | 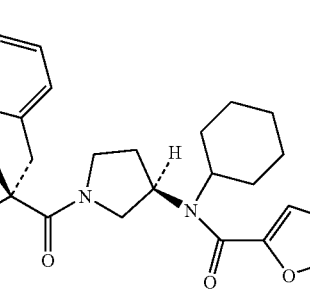 | 81% | 604 | 1.59 |
| 20 | 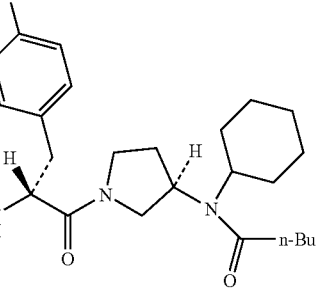 | 25% | 579 | 1.69 |

TABLE 2-continued

| Example Number | Structure | Isolated Yield | MS (ESI) | $t_R$ (min) |
| --- | --- | --- | --- | --- |
| 21 | 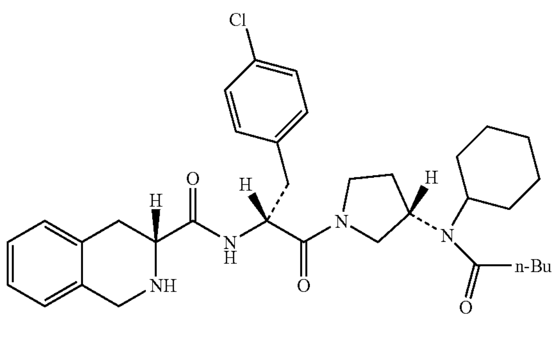 | 24% | 579 | 1.77 |
| 22 | 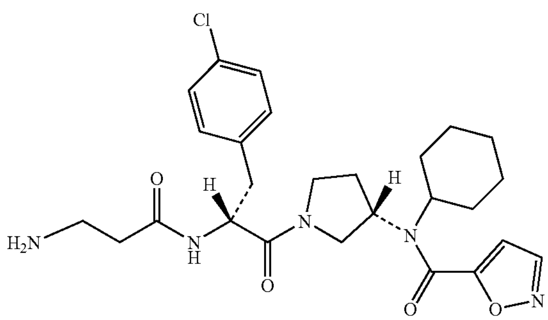 | 25% | 516 | 1.51 |
| 23 | 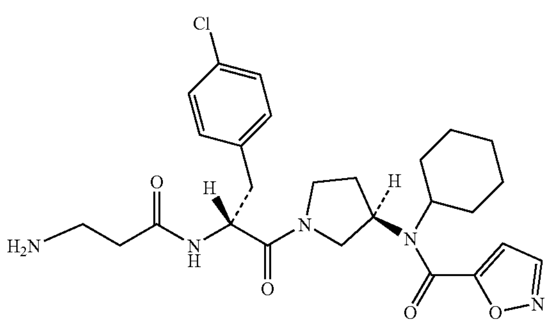 | 21% | 516 | 1.49 |
| 24 | 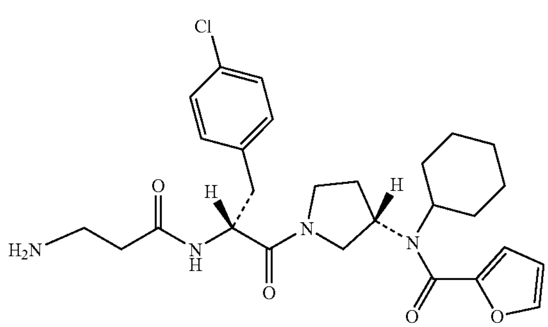 | 20% | 515 | 1.61 |

TABLE 2-continued

| Example Number | Structure | Isolated Yield | MS (ESI) | $t_R$ (min) |
|---|---|---|---|---|
| 25 | 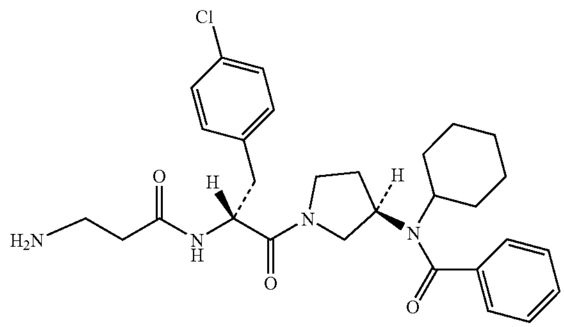 | 10% | 525 | 1.66 |
| 26 | 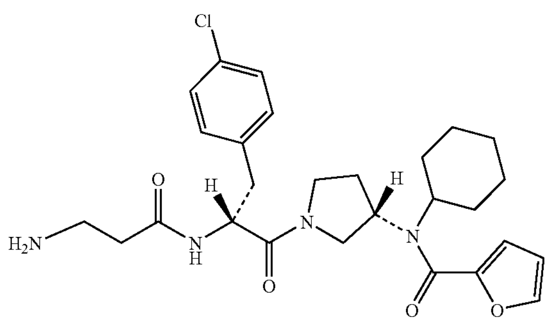 | 99% | 515 | 1.65 |
| 27 | 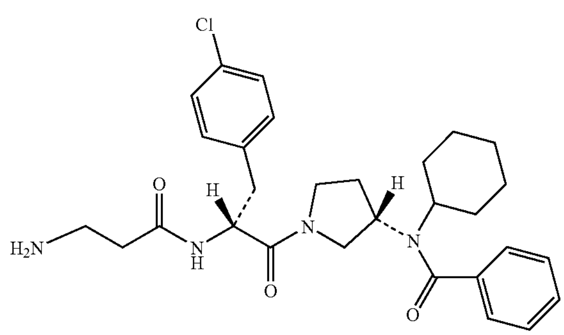 | 84% | 525 | 1.71 |
| 28 | 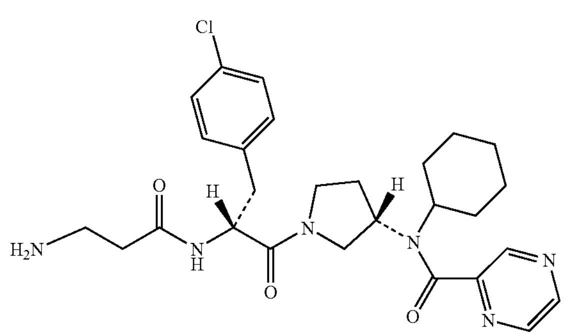 | 96% | 527 | 1.46 |

TABLE 2-continued

| Example Number | Structure | Isolated Yield | MS (ESI) | $t_R$ (min) |
|---|---|---|---|---|
| 29 | 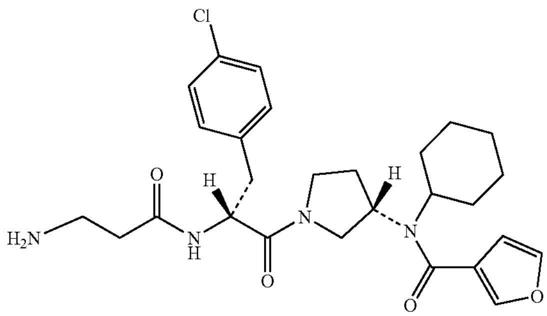 | 96% | 515 | 1.57 |
| 30 | 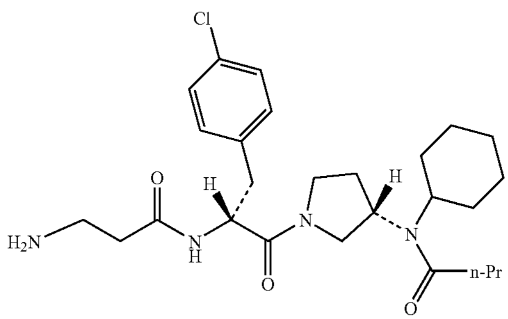 | 54% | 491 | 1.64 |
| 31 | 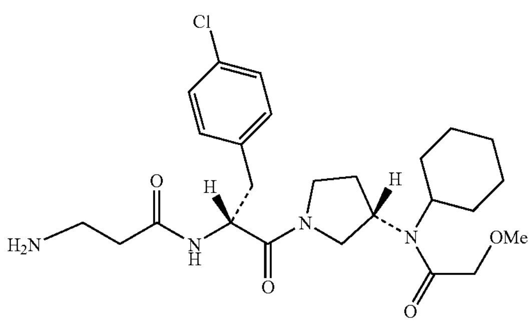 | 26% | 493 | 1.47 |
| 32 | 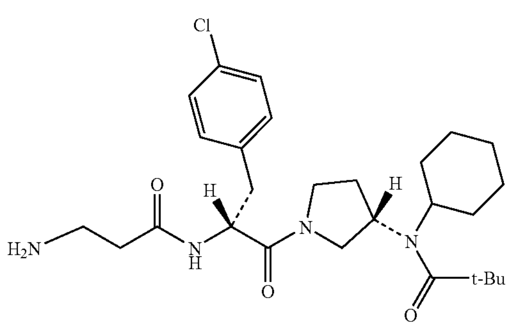 | 50% | 505 | 1.71 |

TABLE 2-continued

| Example Number | Structure | Isolated Yield | MS (ESI) | $t_R$ (min) |
|---|---|---|---|---|
| 33 | 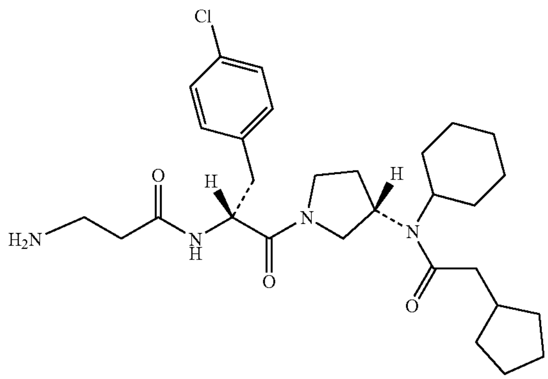 | 24% | 531 | 1.81 |
| 34 | 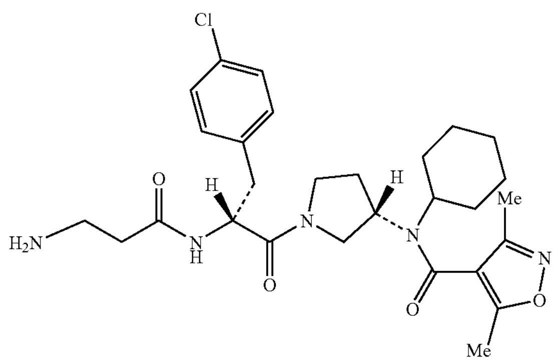 | 37% | 544 | 1.51 |
| 35 | 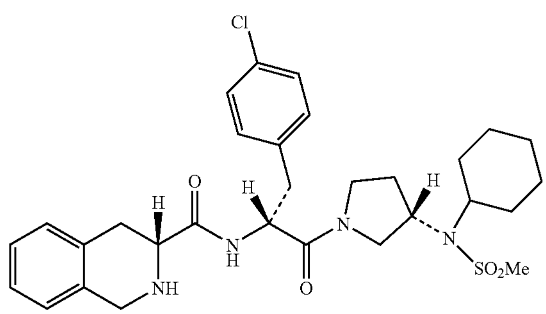 | 84% | 587 | 1.50 |
| 36 | 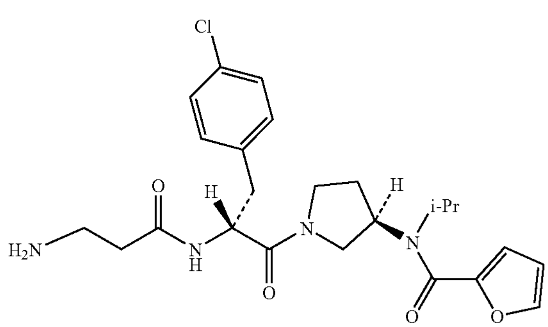 | 81 | 475 | 1.52 |

TABLE 2-continued

| Example Number | Structure | Isolated Yield | MS (ESI) | $t_R$ (min) |
|---|---|---|---|---|
| 37 | 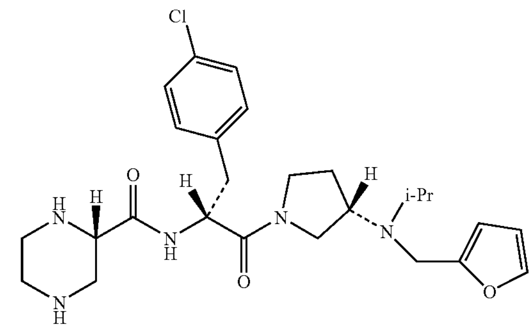 | 82 | 516 | 1.43 |
| 38 | 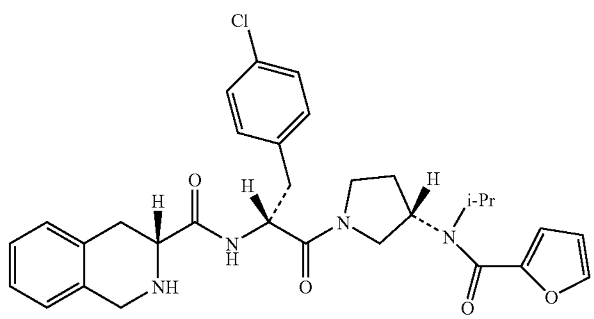 | 76% | 563 | 1.53 |
| 39 | 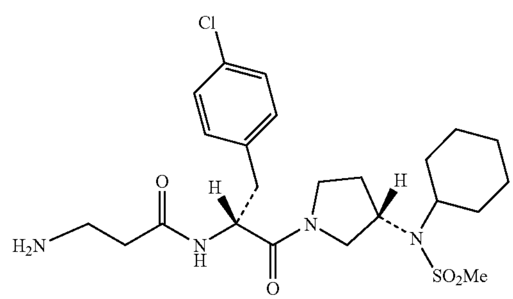 | 76% | 499 | 1.55 |
| 40 | 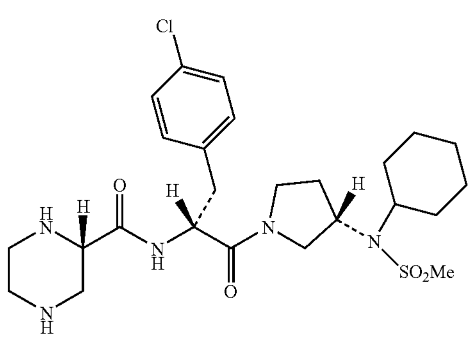 | 84% | 540 | 1.47 |

TABLE 2-continued

| Example Number | Structure | Isolated Yield | MS (ESI) | $t_R$ (min) |
|---|---|---|---|---|
| 41 | 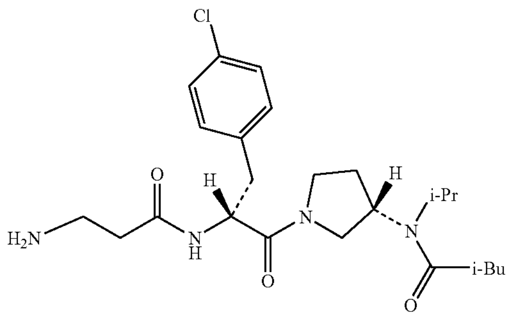 | | 565 | 1.63 |
| 42 | 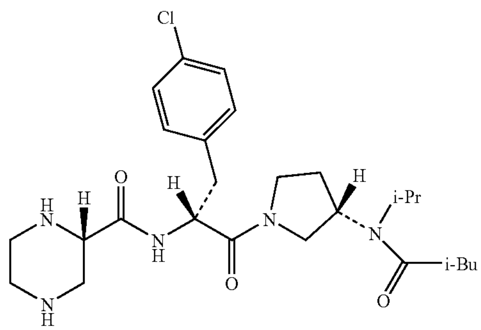 | 84% | 506 | 1.55 |
| 43 | 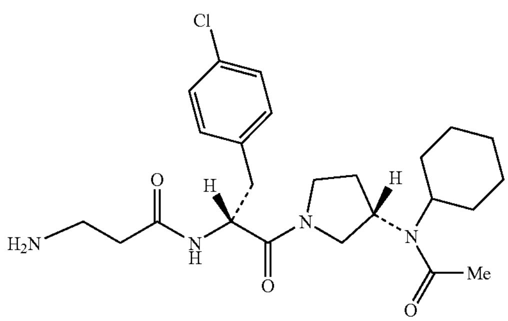 | 82% | 463 | 1.64 |
| 44 | 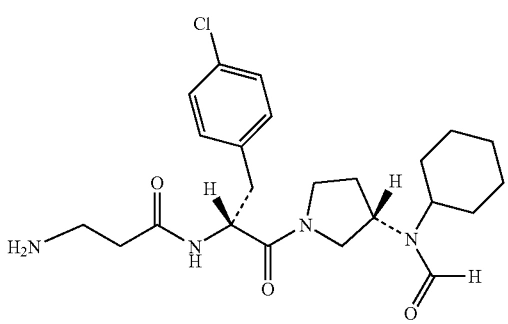 | 82% | 449 | 1.55 |

TABLE 2-continued

| Example Number | Structure | Isolated Yield | MS (ESI) | $t_R$ (min) |
|---|---|---|---|---|
| 45 | 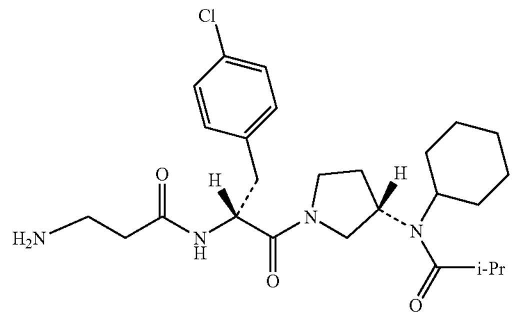 | 80% | 491 | 1.87 |
| 46 | 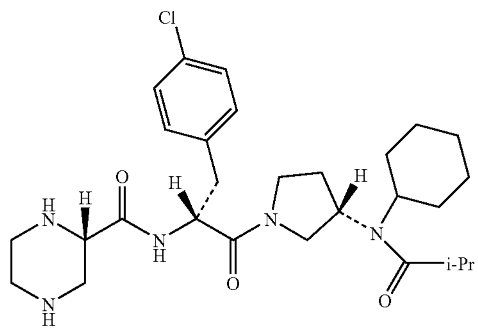 | 85% | 532 | 1.70 |
| 47 | 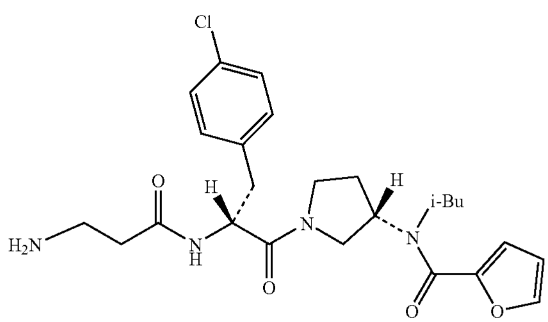 | 54% | 489 | 1.35 |
| 48 | 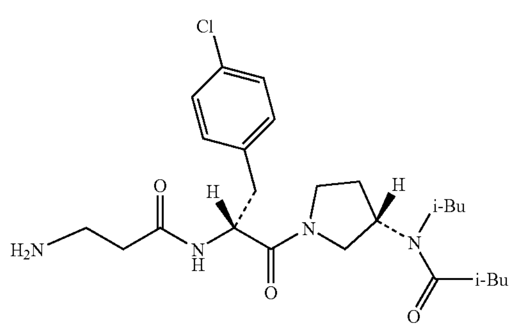 | 54% | 479 | 1.47 |

TABLE 2-continued

| Example Number | Structure | Isolated Yield | MS (ESI) | $t_R$ (min) |
|---|---|---|---|---|
| 49 | 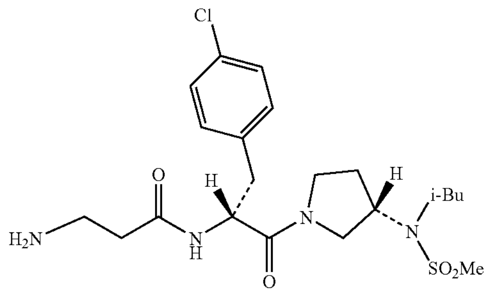 | 10% | 473 | 1.29 |
| 50 | 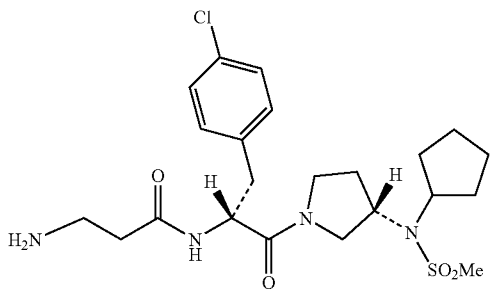 | 11% | 485 | 1.26 |
| 51 | 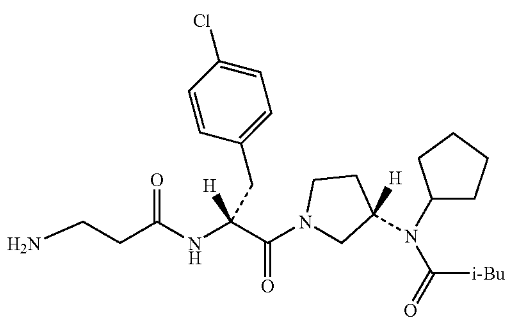 | 34% | 491 | 1.50 |
| 52 | 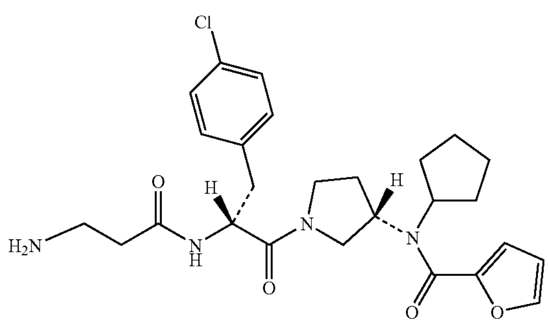 | 12& | 501 | 1.43 |
| 53 | 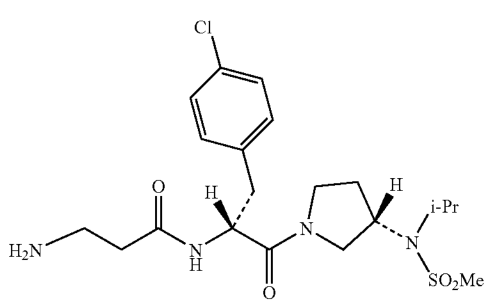 | 81% | 459 | 1.20 |

TABLE 2-continued

| Example Number | Structure | Isolated Yield | MS (ESI) | $t_R$ (min) |
|---|---|---|---|---|
| 54 | 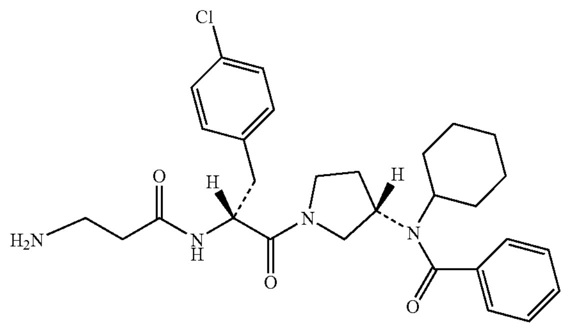 | 28% | 561 | 1.49 |
| 55 | 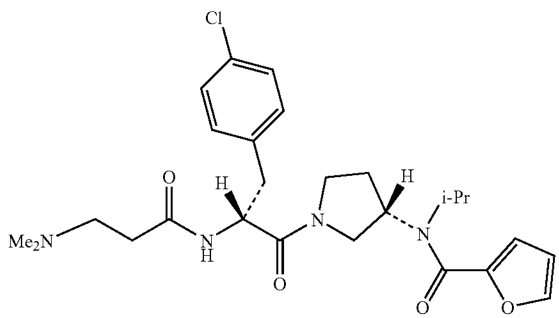 | 70% | 503 | 1.52 |
| 56 | 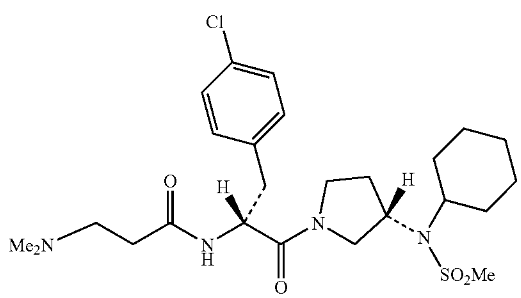 | 72% | 527 | 1.43 |
| 57 | 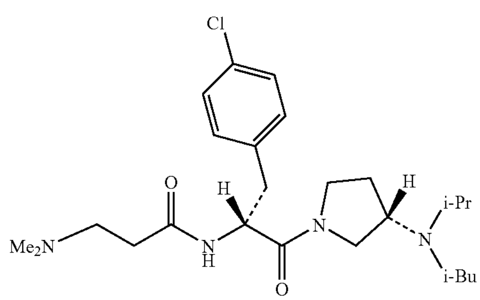 | 72% | 493 | 1.64 |
| 58 | 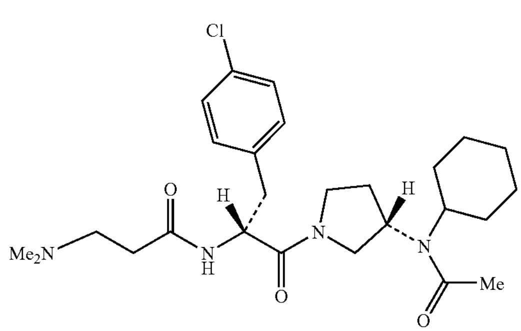 | 73% | 491 | 1.63 |

TABLE 2-continued

| Example Number | Structure | Isolated Yield | MS (ESI) | $t_R$ (min) |
|---|---|---|---|---|
| 59 | 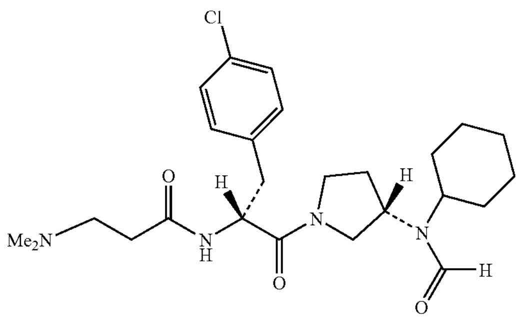 | 73% | 477 | 1.54 |
| 60 | 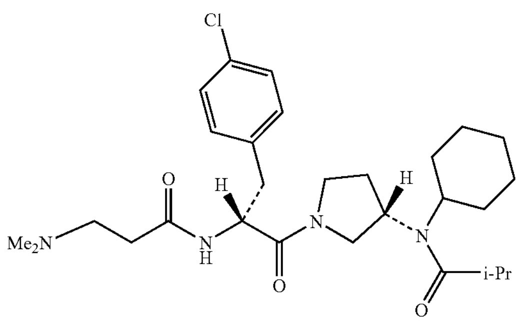 | 80% | 519 | 1.77 |
| 61 | 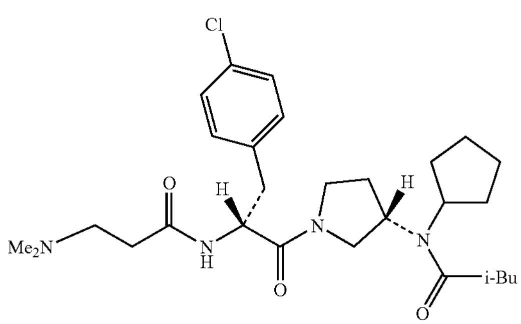 | 22% | 519 | 1.39 |
| 62 | 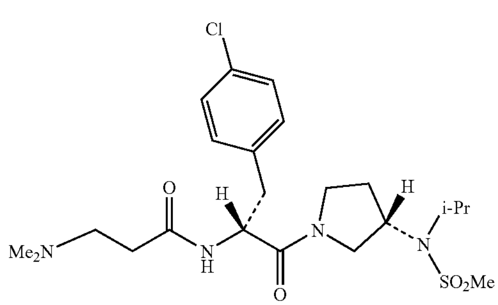 | 76% | 487 | 1.21 |

TABLE 2-continued

| Example Number | Structure | Isolated Yield | MS (ESI) | $t_R$ (min) |
|---|---|---|---|---|
| 63 | 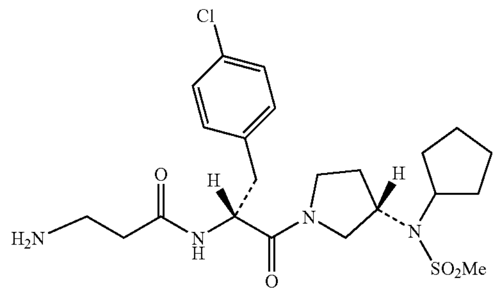 | 42% | 513 | 1.18 |
| 64 | 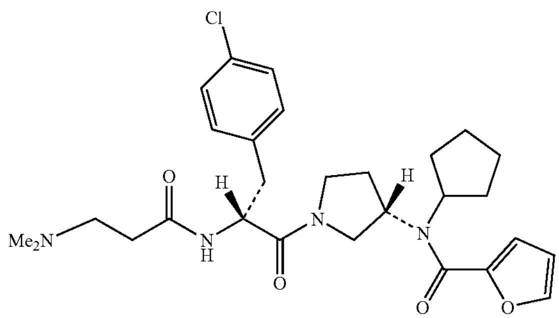 | 19% | 529 | 1.36 |
| 65 | 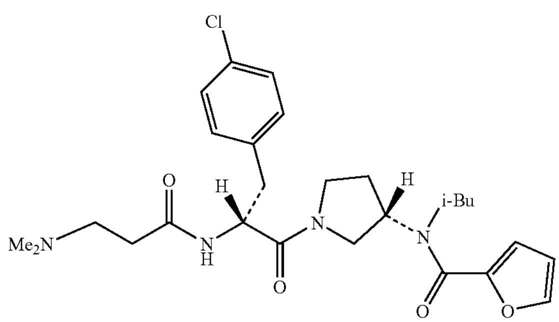 | 17% | 517 | 1.32 |
| 66 | 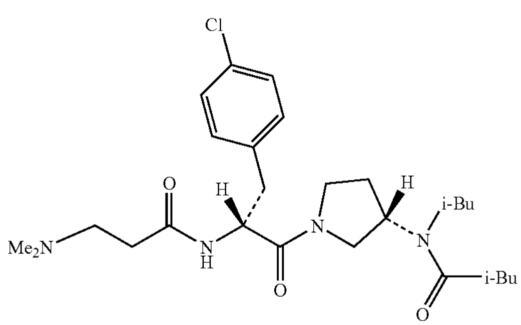 | 44% | 507 | 1.43 |
| 67 | 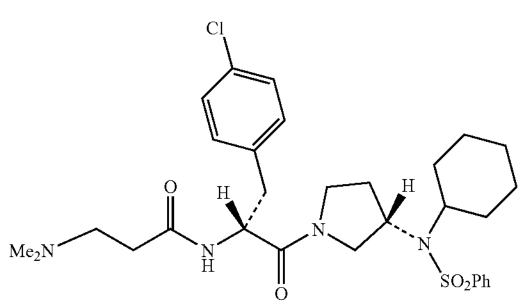 | 10% | 589 | 1.83 |

TABLE 2-continued

| Example Number | Structure | Isolated Yield | MS (ESI) | $t_R$ (min) |
|---|---|---|---|---|
| 68 | 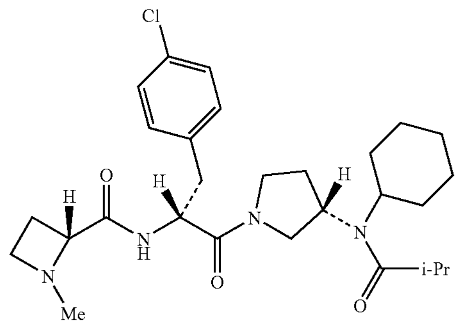 | 80% | 517 | 1.63? |
| 69 | 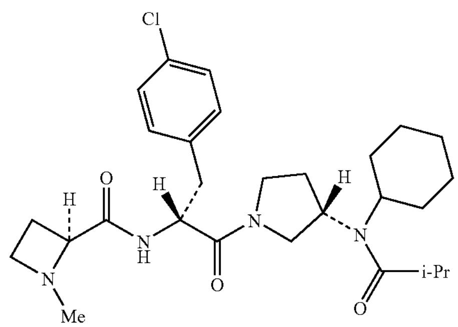 | 14% | 517 | 1.45? |

We claim:

1. A compound of Formula I

I

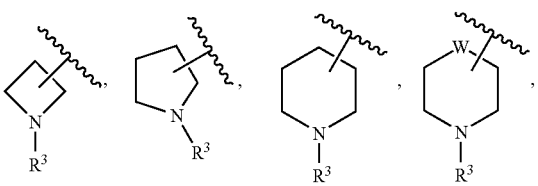

wherein:

A is hydrogen, $C_{1-4}$alkyl, $C_{1-4}$aminoalkyl, or a heterocycle selected from the group consisting of

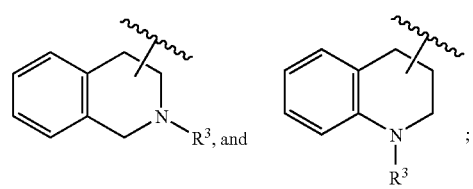

W is $NR^3$, O, or S;

$R^1$ is selected from phenyl, naphthyl, benzfuranyl, benzthienyl, and indolyl moieties that are unsubstituted or substituted with 1 to 2 substituents selected from halo, alkyl, alkyloxy, cyano, trifluoromethyl, and alkoxycarbonyl;

$R^2$ is $C_{1-6}$alkyl or $C_{3-7}$cycloalkyl;

$R^3$ is hydrogen or $C_{1-6}$alkyl;

m is 0, 1, 2, or 3;

n is 1 or 2;

X is CO or $SO_2$;

B is selected from $C_{1-6}$alkyl, $C_{3-7}$cycloalkyl, $C_{3-7}$cycloalkylmethyl; $C_{1-3}$methoxyalkyl, and $C_{1-3}$phenoxyalkyl or is selected from phenyl, naphthyl, pyridinyl, pyrimidinyl, pyridazinyl, pyrazinyl, furanyl, thienyl, pyrrolyl, oxazolyl, isoxazolyl, benzfuranyl, benzthienyl, indolyl, benzoxazolyl, and indazolyl moieties that are unsubstituted or substituted with 1 to 2 substituents selected from halo, alkoxy, uydroxy, trifluoromethyl, cyano, and —$N(R^3)_2$;

or a pharmaceutically acceptable salt or solvate.

2. A compound of the following formula where the carbon marked with an asterisk is of the (R) stereochemistry

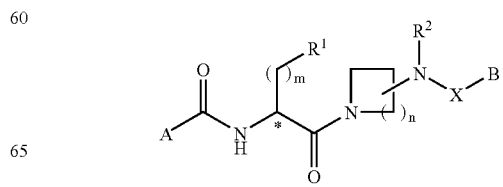

wherein:

A is hydrogen, $C_{1-4}$alkyl, $C_{1-4}$aminoalkyl, or a heterocycle selected from the group consisting of

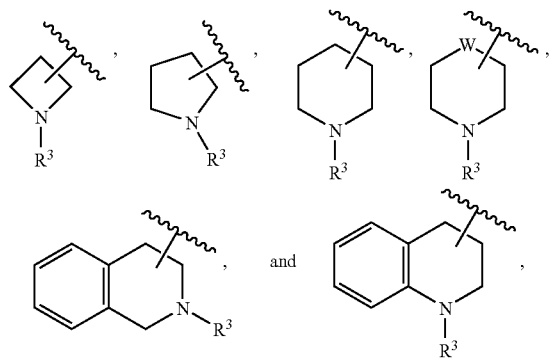

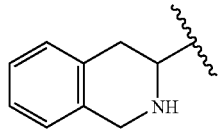

W is $NR^3$, O, or S;
$R^1$ is selected from phenyl, naphthyl, benzfuranyl, benzthienyl, and indolyl moieties that are unsubstituted or substituted with 1 to 2 substituents selected from halo, alkyl, alkyloxy, cyano, trifluoromethyl and alkoxycarbonyl;
$R^2$ is $C_{1-6}$alkyl or $C_{3-7}$cycloalkyl;
$R^3$ is hydrogen or $C_{1-6}$alkyl;
m is 0, 1, 2, or 3;
n is 1 or 2;
X is CO or $SO_2$;
B is selected from $C_{1-6}$alkyl, $C_{3-7}$cycloalkyl, $C_{3-7}$cycloalkylmethyl; $C_{1-3}$methoxyalkyl, and $C_{1-3}$phenoxyalkyl or is selected from phenyl, naphthyl, pyridinyl, pyrimidinyl, pyridazinyl, pyrazinyl, furanyl, thienyl, pyrrolyl, oxazolyl, isoxazolyl, benzfuranyl, benzthienyl, indolyl, benzoxazolyl and indazolyl moieties that are unsubstituted or substituted with 1 to 2 substituents selected from halo, alkoxy, hydroxyl, trifluoromethyl, cyano, and $-N(R^3)_2$;
or a pharmaceutically acceptable salt or solvate.

3. A compound of claim 1 where A is $C_{1-4}$aminoalkyl, or a heterocycle selected from

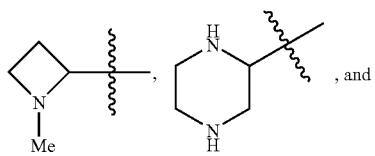

4. A compound of claim 1 where m is 1 and $R^1$ is phenyl substituted with 1–2 substituents selected from halo, alkyl, alkyloxy, cyano, carboalkoxy.

5. A compound of claim 1 where X is CO and B is selected from $C_{1-6}$alkyl, $C_{3-7}$cycloalkyl, $C_{3-7}$cycloalkylmethyl, $C_{1-3}$methoxyalkyl, and $C_{1-3}$phenoxyalkyl or is selected from phenyl, pyrazinyl, furanyl, isoxazolyl, and benzthienyl, moieties that are unsubstituted or substituted with 1 to 2 substituents selected from halo, alkoxy, hydroxy, trifluoromethyl, cyano, and $-N(R^3)_2$.

6. A compound of claim 1 where n is 1.

7. The compound of claim 6: N-[1-[(2R)-3-(4-Chlorophenyl)-2-[[3-(dimethylamino)-1-oxopropyl]amino]-1-oxopropyl]-3-azetidinyl]-N-cyclohexyl-3-methyl-butanamide.

8. A compound of claim 1 where n is 2.

9. A compound of claim 8 selected from the following group:
- (3R)-N-[(1R)-1-[(4-Chlorophenyl)methyl]-2-[3-[cyclohexyl(5-isoxazolylcarbonyl)amino]-1-pyrrolidinyl]-2-oxoethyl]-1,2,3,4-tetrahydro-3-isoquinolinecarboxamide;
- (3R)-N-[(1R)-1-[(4-Chlorophenyl)methyl]-2-[(3S)-3-[cyclohexyl(5-isoxazolylcarbonyl)amino]-1-pyrrolidinyl]-2-oxoethyl]-1,2,3,4-tetrahydro-3-isoquinolinecarboxamide;
- (2S)-N-[(1R)-1-[(4-Chlorophenyl)methyl]-2-[(3S)-3-[cyclohexyl(1-oxopentyl)amino]-1-pyrrolidinyl]-2-oxoethyl]-1,2,3,4-tetrahydro-3-isoquinolinecarboxamide;
- (3R)-N-[(1R)-1-[(4-Chlorophenyl)methyl]-2-[(3S)-3-[cyclohexyl(2-furanylcarbonyl)amino]-1-pyrrolidinyl]-2-oxoethyl]-1,2,3,4-tetrahydro-3-isoquinolinecarboxamide;
- N-[1-[(2R)-3-(4-Chlorophenyl)-2-[(3S)-[3-(dimethylamino)-1-oxopropyl]amino]-1-oxopropyl]-3-pyrrolidinyl]-N-cyclohexyl-3-methyl-butanamide; and
- (3R)-N-[(1R)-1-[(4-Chlorophenyl)methyl]-2-[(3S)-3-[cyclohexyl(methylsulfonyl)amino]-1-pyrrolidinyl]-2-oxoethyl]-1,2,3,4-tetrahydro-3-isoquinolinecarboxamide.

10. A pharmaceutical composition comprising a therapeutic amount of a compound of claim 1 and a pharmaceutically acceptable carrier.

* * * * *